(12) United States Patent
Nielsen et al.

(10) Patent No.: US 8,124,085 B2
(45) Date of Patent: Feb. 28, 2012

(54) BISPECIFIC BINDING AGENTS FOR MODULATING BIOLOGICAL ACTIVITY

(75) Inventors: Ulrik B. Nielsen, Quincy, MA (US); Birgit M. Schoeberl, Cambridge, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 766 days.

(21) Appl. No.: 11/579,350

(22) PCT Filed: May 5, 2005

(86) PCT No.: PCT/US2005/015639
§ 371 (c)(1),
(2), (4) Date: Sep. 29, 2008

(87) PCT Pub. No.: WO2005/117973
PCT Pub. Date: Dec. 15, 2005

(65) Prior Publication Data
US 2009/0181022 A1 Jul. 16, 2009

Related U.S. Application Data

(60) Provisional application No. 60/568,656, filed on May 5, 2004.

(51) Int. Cl.
*A61K 39/00* (2006.01)
*A61K 39/395* (2006.01)
(52) U.S. Cl. .................... 424/136.1; 424/138.1
(58) Field of Classification Search .......... None
See application file for complete search history.

(56) References Cited

U.S. PATENT DOCUMENTS

| | | | |
|---|---|---|---|
| 7,332,580 B2 | 2/2008 | Adams et al. | |
| 7,332,585 B2 | 2/2008 | Adams et al. | |
| 2002/0103345 A1* | 8/2002 | Zhu | 530/388.15 |
| 2004/0071696 A1 | 4/2004 | Adams et al. | |
| 2004/0086503 A1* | 5/2004 | Cohen et al. | 424/143.1 |
| 2005/0079184 A1* | 4/2005 | Hsing-Chang et al. | 424/178.1 |

FOREIGN PATENT DOCUMENTS

| | | |
|---|---|---|
| WO | 91/00360 | 1/1991 |
| WO | 95/24220 | 9/1995 |

OTHER PUBLICATIONS

Camirand et al (Med Sci Monit, 2002, 8:BR521-6).*
Dorvillius, et al., "Targeting of human breast cancer by a bispecific antibody directed against two tumor-associated antigens: ErbB-2 and carcinoembryonic antigen," *Tumor Biology*, vol. 23, pp. 337-347 (2002).
Schmidt, et al., "Targeting inhibition of tumor cell growth by a specific single-chain toxin containing an antibody domain and TGFα," *British Journal of Cancer*,vol. 74, pp. 853-862 (1996).
Becerril, et al., "Toward selection of internalizing antibodies from phage libraries," *Biochemical and biophysical Research Communications*, vol. 225, pp. 386-393 (1999).
Francois, et al., "Antibodies directed at mouse IL-2-R alpha and beta chains act in synergy to abolish T-cell proliferation in vitro and delayed type hypersensitivity reaction in vivo," *Transpl. Int.*, vol. 9, pp. 46-50 (1996).
Lu et al., "Complete Inhibition of Vascular Endothelial Growth Factor (VEGF) Activities with a Bifunctional Diabody Directed against Both VEGF Kinase Receptors, *fms*-like Tyrosine Kinase Receptor and Kinase Insert Domain-containing Receptor," 2001, Cancer Research, 61, 7002-7008.
Nielsen, et al., "Targeting of bivalent anti-ErbB2 diabody antibody fragments to tumor cells is independent of the intrinsic antibody affinity," *Cancer Research*, vol. 60, pp. 6434-6440 (Nov. 2000).
Bortoletto, Nicola et al.; "Optimizing anti-CD3 affinity for effective T cell targeting against tumor cells"; 2002, *Eur. J. Immunol.*, vol. 32, pp. 3102-3107.
McCall, Adrian M. et al.; "Increasing the Affinity for Tumor Antigen Enhances Bispecific Antibody Cytotoxicity"; 2001, *Journal of Immunology*, vol. 166, No. 10, pp. 6112-6117.

* cited by examiner

*Primary Examiner* — Laura B Goddard
(74) *Attorney, Agent, or Firm* — Kilpatrick Townsend & Stockton LLP

(57) ABSTRACT

Methods for improving the biological and pharmaceutical properties of bispecific binding agents are described herein where the bispecific binding agent are able to target cells by a high affinity binding domain to a first cell surface marker that does not induce a significant biological effect and a low affinity binding domain that binds specifically to a second cell surface marker, causing a significant and desired biological effect. Compositions of such bispecific binding agents, uses for them, and kits containing them are also provided.

9 Claims, No Drawings

BISPECIFIC BINDING AGENTS FOR MODULATING BIOLOGICAL ACTIVITY

CROSS-REFERENCES TO RELATED APPLICATIONS

This application claims the benefit of U.S. Provisional Application No. 60/568,656, filed May 5, 2004, the contents of which are hereby incorporated by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Many diseases and disorders are caused by inappropriate or excessive activation of signal transduction pathways caused by activation of cell surface receptors, e.g., by the binding of receptor-specific ligands. Receptors involved in the initiation or progression of diseases and disorders, such as cancer and autoimmune disorders, have emerged as prime targets for the development of therapeutics that reduce or prevent receptor activation. Examples of target receptors include, e.g., the epidermal growth factor receptor ("EGFR"), the insulin-like growth factor 1 receptor ("IGF1-R"), and the platelet-derived growth factor receptor ("PDGFR"), which tend to be overexpressed or aberrantly activated in many disease states, such as in the most common solid tumors, including non-small cell lung cancer and cancers of the breast, prostate, and colon, and in many autoimmune disease, such as myasthenia gravis, systemic lupus erythematosus, and rheumatoid arthritis. Activation of the receptor results in autophosphorylation, which drives signal transduction pathways that lead to disease progression.

Seminal studies with receptor inhibitors have clearly demonstrated that by preventing the activation of a receptor associated with a disease state the development of that disease state can be altered. Generally, though, the receptor or receptors responsible for the disease state are expressed on many different cells and tissues in addition to the diseased cells or tissues. Although receptor inhibitors, e.g., Herceptin®, which targets ErbB2 ("HER-2"), are becoming available for clinical use, new challenges include identifying a therapeutic agent that will effectively target the diseased cells or tissue without targeting non-affected cells and tissues.

One approach to targeting agents specifically to diseased cells has been the use of bispecific binding agents, sometimes referred to herein as "bsBAs". Bispecific binding agents comprise two binding domains, each of which specifically recognizes and binds to a separate molecule (for convenience, the molecule specifically bound by each respective binding domain may be referred to as the "ligand" for that binding domain). Bispecific binding agents have been attempted for some time, as exemplified by Schmidt M, et al., "A bivalent single-chain antibody-toxin specific for ErbB-2 and the EGF receptor," Int J Cancer, 65 (4):538-46 (1996), Lu D, et al., "Simultaneous blockade of both the epidermal growth factor receptor and the insulin-like growth factor receptor signaling pathways in cancer cells with a fully human recombinant bispecific antibody," J Biol Chem. 279 (4):2856-65 (2004), and Francois C, et al., "Antibodies directed at mouse IL-2-R alpha and beta chains act in synergy to abolish T-cell proliferation in vitro and delayed type hypersensitivity reaction in vivo," Transpl Int. 9 (1):46-50 (1996). Because bsBAs often use antibodies as one or both of the binding domains, bsBAs are sometimes included in the class of agents referred to as immunotherapeutics.

Unfortunately, the universe of molecules that can be used as targets for bsBAs is limited. Only a relatively small number of molecules are expressed on diseased cells but not on normal cells, and which therefore can be used to target agents exclusively to diseased cells. An additional number of molecules are expressed in greater numbers on diseased cells than on normal cells. These molecules can permit some preferential delivery of agents to diseased cells over normal cells, depending on the degree to which the molecule is overexpressed in diseased cells compared to normal cells.

Even with substantial overexpression of the target molecule on target cells, however, delivery of targeted therapeutic agents have often been accompanied by adverse side effects due to binding of the agent to normal cells expressing the target molecule. For example, the HER2 (erbB2) receptor that is the target for the FDA-approved immunotherapeutic agent Herceptin®, is overexpressed at levels some 10 to 100 times more than the expression of the HER2 receptor in non-cancer cells. Nonetheless, a percentage of patients develop cardiac arrhythmia and other adverse side effects due to binding of Herceptin® to normal cells.

Thus, it would be desirable to increase the therapeutic window of immunotherapeutic agents by developing bsBAs with an improved ability to bind to target cells without binding to non-target cells.

SUMMARY OF THE INVENTION

The present invention provides new compositions of bispecific binding agents, as well as kits comprising them and methods and uses for them.

In a first group of embodiments, the invention provides methods for modulating a biological activity of a target cell using a bispecific binding agent (i) having a first binding domain having a Kd for a first target molecule on the surface of said cell of $10^{-7}$ M or less and a second binding domain having a Kd for a second target molecule on the surface of said cell, (ii) which second target molecule is different than said first target molecule, (iii) wherein said affinity of said second binding domain for said second target molecule is at least 10 times greater than the Kd of said first binding domain to said first target molecule, and (iv) further wherein when the target molecule of said first binding domain is ErbB2, the target molecule for said second binding domain is not ErbB3, comprising contacting the bispecific binding agent with the target cell under conditions that permit the first and second binding domains to bind to the first and second target molecules, respectively, wherein binding of the second binding domain to the second target molecule modulates the biological activity of the second target molecule, thereby modulating a biological activity of the target cell, and further wherein binding of said first binding domain to the first target molecule does not modulate a biological activity of the target cell. In some embodiments, the bispecific binding agent comprises two antibodies. In some embodiments, the antibodies are diabodies, two single chain Fvs connected directly or by a linker, disulfide stabilized Fvs, or combinations thereof. In some embodiments, the target cell is a cancer cell. In some embodiments, the first target molecule is a tumor-associated antigen, cytokine receptor, or growth factor receptor. In some embodiments, the tumor-associated antigen is selected from the group consisting of MART-1, gp100, and MAGE-1. In some embodiments, the first target molecule is selected from the group consisting of carcinoembryonic antigen (CEA), ErbB2, EGFR, LewisY, MUC-1, EpCAM, CA125, prostate specific membrane antigen (PSMA), and TAG72. In some embodiments, the second target molecule is selected from the group consisting of ErbB3, ErbB4, any of FGF receptors 1-4, HGF receptor, IGF1-R, PDGF, receptors alpha and beta, and C-KIT. In some embodiments, the target cell is a breast cancer cell and the target molecule is a receptor tyrosine kinase selected from the group consisting of: epidermal growth factor receptor (EGFR), ErbB2 (HER2/neu), ErbB3 (HER3) and ErbB4 (HER4). In some embodiments, the Kd of the first binding domain to the first target molecule is between $10^{-8}$ and $10^{-12}$ M. In some embodiments, the Kd of the second binding domain to the second target molecule is at least 20 times greater than the Kd of the first binding domain to the first target molecule.

The invention further provides methods for modulating biological activity of a target molecule on a target cell in an organism having target and non-target cells, wherein the target cells have a first target molecule on their exterior and a second target molecule on their exterior surface, and wherein (i) the first and second target molecules do not share a common ligand, (ii) the first target molecule is at least 10 times more abundant on the surface of the target cells than on non-target cells that also bear the second target molecule, (iii) the second target molecule has a biological activity, but the first target molecule does not, and (iv) when the target molecule of the first binding domain is ErbB2 (HER2), the target molecule for the second binding domain is not ErbB3 (HER3), comprising using a bispecific binding agent having a first binding domain having a dissociation constant (Kd) for the first target molecule of $10^{-7}$ M or less and a second binding domain having a Kd for the second target molecule that is at least 10 times greater than the Kd of the first binding domain, and contacting the bispecific binding agent with a target cell under conditions that permit the first and second binding domains to bind to the first and second target molecules, respectively, wherein the binding of said second binding domain modulates the biological activity of said second target molecule on said target cell. In some embodiments, the bispecific binding agent comprises two antibodies. In some embodiments, the antibodies are diabodies, two single chain Fvs connected directly or by a linker, disulfide stabilized Fvs, or combinations thereof. In some embodiments, the target cell is a cancer cell. In some embodiments, the target molecule is a tumor-associated antigen, cytokine receptor, or growth factor receptor. In some embodiments, the tumor-associated antigen is selected from the group consisting of MART-1, gp100, and MAGE-1. In some embodiments, the first target molecule is selected from the group consisting of carcinoembryonic antigen (CEA), ErbB2, EGFR, LewisY, MUC-1, EpCAM, CA125, prostate specific membrane antigen (PSMA), and TAG72. In some embodiments, the second target molecule is selected from the group consisting of ErbB3, ErbB4, any of FGF receptors 1-4, HGF receptor, IGF1-R, PDGF, receptors alpha and beta, and C-KIT. In some embodiments, the Kd of the first binding domain for the first target molecule is between $10^{-8}$ M and $10^{-12}$ M. In some embodiments, the Kd of the second binding domain to the second target molecule is at least 20 times greater than the Kd of the first binding domain to the first target molecule. In some embodiments, the Kd of the second binding domain to the second target molecule is at least 50 times greater than the Kd of the first binding domain to the first target molecule. In some embodiments, the modulation is a decrease in the activity of a receptor tyrosine kinase.

In another group of embodiments, the invention provides bispecific binding agents (bsBAs) comprising a first binding domain having a dissociation constant (Kd) of $10^{-7}$ M or less for a first target molecule on a target cell and a second binding domain having a Kd for a second target molecule on a target cell which Kd is at least 10 times greater than the Kd of the first binding domain for the first target molecule, wherein (i) the first and second target molecules do not have the same natural ligand, (ii) the second target molecule, but not the first target molecule, has a biological activity, and (iii) when the target molecule of the first binding domain is ErbB2 (HER2), the target molecule for the second binding domain is not ErbB3 (HER3), and further wherein the second binding domain, when bound to the second target molecule, modulates the biological activity of the second target molecule. In some embodiments, the Kd of the second binding domain is more than 50 times greater than the Kd of the first binding domain. In some embodiments, the Kd of the second binding domain is 100 or more times greater than the Kd of the first binding domain. In some embodiments, The bsBA comprises two antibodies. In some of these embodiments, the antibodies are diabodies, two single chain Fvs connected directly or by a linker, disulfide stabilized Fvs, or combinations thereof. In some embodiments, the first binding domain binds to a tumor-associated antigen, cytokine receptor, or growth factor receptor. In some embodiments, the first target molecule is selected from the group consisting of carcinoembryonic antigen (CEA), ErbB2, EGFR, LewisY, MUC-1, EpCAM, CA125, prostate specific membrane antigen (PSMA), and TAG72. In some embodiments, the second target molecule is selected from the group consisting of ErbB3, ErbB4, any of FGF receptors 1-4, HGF receptor, IGF1-R, PDGF, receptors alpha and beta, and C-KIT. In some embodiments, the Kd of the first binding domain is between $10^{-8}$ and $10^{-12}$ M. In some embodiments, the first target molecule is overexpressed by at least 10 times on target cells as compared to its expression on normal cells.

In still another group of embodiments, the invention provides compositions of (a) a bispecific binding agent (bsBA) comprising a first binding domain having a dissociation constant (Kd) for a first target molecule on a target cell of $10^{-7}$ M or less and a second binding domain having a Kd for a second target molecule on a target cell that is at least 10 times greater than the Kd of the first binding domain, wherein the first and second target molecules do not have the same natural ligand, and wherein (i) the second target molecule, but not the first target molecule, has a biological activity, (ii) the second binding domain, when bound to the second target molecule, modulates the biological activity of the second target molecule and (iii) when the target molecule of the first binding domain is ErbB2 (HER2), the target molecule for the second binding domain is not ErbB3 (HER3), and (b) a pharmaceutically acceptable carrier. In some embodiments, the Kd of the second binding domain is more than 50 times greater than the Kd of the first binding domain. In some embodiments, the Kd of the second binding domain is 100 or more times greater than the Kd of the first binding domain. In some embodiments, the bsBA comprises two antibodies. In some embodiments, the antibodies are diabodies, two single chain Fvs connected directly or by a linker, disulfide stabilized Fvs, or combinations thereof. In some embodiments, the first binding domain binds to a tumor-associated antigen, cytokine receptor, or growth factor receptor. In some embodiments, the first target molecule is selected from the group consisting of carcinoembryonic antigen (CEA), ErbB2, EGFR, LewisY, MUC-1, EpCAM, CA125, prostate specific membrane antigen (PSMA), and TAG72. In some embodiments, the second target molecule is selected from the group consisting of ErbB3, ErbB4, any of FGF receptors 1-4, HGF receptor, IGF1-R, PDGF, receptors alpha and beta, and C-KIT. In some embodiments, the first target molecule is overexpressed by at least 10 times on target cells than on non-target cells that also bear the second target molecule. In some embodiments, In another group of embodiments, the invention provides uses of a bispecific binding agent (bsBA) comprising a first binding domain having a dissociation constant (Kd) for a first target molecule on a target cell of $10^{-7}$ M or less and a second binding domain having a Kd for a second target molecule on a target cell that is at least 10 times greater than the Kd of the first binding domain, wherein (i) the first and second target molecules do not have the same natural ligand, (ii) the second target molecule, but not said first target molecule, has a biological activity, (iii) the second binding domains when bound to the second target molecule, modulates the biological activity of the second target molecules, and (iv) when the target molecule of said first binding domain is ErbB2, the target molecule for the second binding domain is not ErbB3, for the manufacture of a medicament. In some embodiments, the Kd of said second binding domain is more than 50 times greater than the Kd of the first binding domain. In some embodiments, the Kd of said second binding domain is 100 or more times greater than the Kd of the first binding domain. In some embodiments, the bsBA comprises two antibodies. In some embodiments, the antibodies are diabodies, two single chain Fvs connected directly or by a linker, disulfide stabilized Fvs, or combinations thereof. In some embodiments, the target molecules bound by the first binding domain and by the second binding domain are independently selected from the group consisting of a tumor-associated antigen, a cytokine receptor, and a growth factor receptor, provided that the first binding domain and the second binding domain do not bind the same tumor-associated antigen, cytokine receptor, or growth factor receptor. In some embodiments, the medicament is for inhibiting the proliferation of cancer cells. In some embodiments, the first target molecule is overexpressed by at least 10 times on target cells than on non-target cells that also bear the second target molecule.

Further, the invention provides kits comprising (a) a container, and (b) a bispecific binding agent (bsBA) comprising a first binding domain having a dissociation constant (Kd) of $10^{-7}$ M or less for a first target molecule on a target cell and a second binding domain having a Kd for a second target molecule on a target cell which Kd is at least 10 times greater than the Kd of the first binding domain for the first target molecule, wherein (i) the first and second target molecules do not have the same natural ligand, (ii) the second target molecule, but not the first target molecule, has a biological activity, (iii) the second binding domain, when bound to the second target molecule, modulates the biological activity of the second target molecule, and (iv) when the target molecule of the first binding domain is ErbB2 (HER2), the target molecule for said second binding domain is not ErbB3 (HER3). In some embodiments, the Kd of the second binding domain is more than 50 times greater than the Kd of the first binding domain. In some embodiments, the Kd of the second binding domain is 100 or more times greater than the Kd of the first binding domain. In some embodiments, the bsBA comprises two antibodies. In some embodiments, the antibodies are diabodies, two single chain Fvs connected directly or by a linker, disulfide stabilized Fvs, or combinations thereof. In some embodiments, the first binding domain binds to a tumor-associated antigen, cytokine receptor, or growth factor receptor. In some embodiments, the first target molecule is selected from the group consisting of carcinoembryonic antigen (CEA), ErbB2, EGFR, LewisY, MUC-1, EpCAM, CA125, prostate specific membrane antigen (PSMA), and TAG72. In some embodiments, the second target molecule is selected from the group consisting of ErbB3, ErbB4, any of FGF receptors 1-4, HGF receptor, IGF1-R, PDGF, receptors alpha and beta, and C-KIT. In some embodiments, the Kd of the first binding domain is between $10^{-8}$ and $10^{-12}$ M. In some embodiments, the first target molecule is overexpressed by at least 10 times on target cells as compared to its expression on normal cells.

DETAILED DESCRIPTION OF THE INVENTION

Introduction

One problem with current immunotherapeutic agents is that their tendency to bind to normal cells as well as to diseased cells causes adverse side effects. Thus, one goal of the scientific community has been to develop immunotherapeutic agents with an improved ability to bind target cells (e.g., disease cells) without also binding non-target cells (that is, normal cells).

The present invention provides compositions and methods for improving the specificity of one class of immunotherapeutic agents for binding target cells. These methods and compositions provide an improved ability to modulate biological activity of target cells without affecting the corresponding activity of non-target cells. Surprisingly, it has now been discovered that the specificity of targeting diseased cells by the immunotherapeutic agents known as bispecific binding agents ("bsBAs") can be increased by controlling the differences in the binding affinities of the two binding domains of the bsBAs. The bsBAs of the invention can then be used for increasing or decreasing the biological activity of a target molecule on the target cells, and thereby provide an improved ability to modulate biological activity of target cells with reduced, if any, effect on the corresponding activity of non-target cells.

As the name implies, bsBAs have two binding domains, each specific for a different target molecule (for convenience, the molecule specifically bound by the binding domain may be referred to as the "ligand" for the binding domain). The first binding domain is generally used to target the bsBA to a cell of choice, sometimes referred to as a "target cell." Thus, this binding domain is also referred to herein as the "targeting domain". In the methods of the present invention, the binding of the targeting domain to its target molecule does not induce a significant biological effect in the target cell. The second binding domain binds to a second target molecule on the target cell. The binding of the second binding domain to its ligand is intended to modulate a specific biological effect (that is, to increase or to inhibit that biological activity). Binding domains with capabilities to modulate biological activities in different ways are known in the art.

Often, the biological activities are inhibited by the binding of the binding domain to its target molecule. For example, if the molecule bound by the binding domain is part of a cytokine receptor, the binding of the binding domain to that receptor can block access of the cytokine to the receptor, thereby inhibiting the biological activity that would otherwise be induced by that binding. Similarly, the binding of the binding domain to the receptor can prevent the receptor from forming a heterodimer, which is required for the full activation of some cytokine receptors such as the interleukin ("IL")-2 receptor. Or, the binding of the binding domain may change the conformation of the receptor so that it cannot bind its natural ligand and thereby be activated. Conversely, the binding domain can be one selected for its ability to increase the biological activity by binding to the receptor. For example, the binding of the binding domain to the receptor can mimic the effect of the natural ligand for the receptor, so that the binding activates the receptor, or the binding of the binding domain may induce a conformational change which causes a low affinity receptor to become a high affinity receptor for its natural ligand.

As noted, the first binding domain of the bsBAs of the invention serves to target the bsBAs to the target cell, while the second serves primarily to induce an effect on the target cell. For convenience in distinguishing the two domains, therefore, the first binding domain is sometimes referred to herein as the "targeting domain," while the second binding domain is sometimes referred to herein as the "effector domain." Similarly, for convenience in distinguishing the molecules bound by the two binding domains, the target molecule for the effector domain will sometimes be referred to as the "effector target molecule," while the term "target molecule" by itself will refer to the target of the targeting domain.

Previous bsBAs have typically been constructed using binding domains with the highest available affinity for each of the respective target molecules. Persons of skill will appreciate that it is unlikely that one domain will have exactly the same affinity for its respective target as does the other, and the two binding domains therefore usually have a difference in affinity. In previous bsBAs, however, the difference in affinities has typically not been great and may or may not be significant in terms of actual effect on binding.

In the methods and compositions of the invention, though, the targeting domain is selected to have at least an order of magnitude higher binding affinity for its ligand than the affinity the effector domain has for its ligand. That is, the targeting domain has at least 10 times or greater affinity for the molecule to which it recognizes and binds than the effector domain has for the molecule to which it recognizes and binds. In some embodiments, the affinity of the targeting domain for its ligand is at least 15 times higher than that of the effector domain, in others it is 20 times or more higher, in other embodiments, it is 25 time or more higher, and in some embodiments, it has an affinity 30, 40, 50 or even 100 times or more higher than that the affinity of the effector domain for its target, with each respective higher affinity being more preferred. Since there is at least an order of magnitude difference in binding affinity between the two binding domains of the bsBAs of the invention, the bsBAs are occasionally referred to herein as "hi-lo" bsBAs.

The intentional and substantial differential in binding affinity between the target binding domain and the effector binding domain provides surprising and previously unrecognized advantages over prior bispecific molecules. As noted above, previously known bispecific agents have had binding moieties with affinities as high as possible for the target ligands. But, bispecific molecules with binding moieties that have similar affinities are limited in the molecules to which they can be targeted and the situations in which they can be used, compared to the compositions and methods of the invention. Some of the advantages of the invention can be considered by referring to a hypothetical example.

Consider the case of a cancer cell which has two receptors, receptor A, which is overexpressed on the cancer cell compared to normal cells, and receptor B, which is expressed on normal cells in about the same number of copies as are present on the cancer cell. A bispecific binding agent with binding domains with approximately equal affinity for both receptors will tend to have roughly equal effects on both cancer cells and on normal, non-cancer cells. This is particularly in the case where high concentrations of bsBAs are achieved, since the bsBAs will tend to saturate both receptors by monovalent binding.

By contrast, a bsBA of the invention, having a higher affinity targeting domain targeted to receptor A and a lower affinity effector domain targeted to receptor B, and having 10, 20, 30, or even more times more affinity for receptor A than for receptor B, will preferentially bind to the cancer cells, and by normal kinetic interactions, will bind in larger numbers to the cancer cells as compared to normal cells. Instead of promiscuously binding to cells bearing receptor B, including substantial numbers of normal cells, therefore, the effector domain will be selectively delivered to the cancer cells. Thus, the invention permits more selective targeting of effector domain to target cells.

Further, the binding of the higher affinity binding domain to receptor A tethers the lower affinity, effector domain in proximity to the cell surface, where it is available to interact with receptor B over time. This permits the effector domain to bind receptor B even though its relatively low affinity for receptor B might not normally be sufficient to hold it to the receptor were the effector domain provided as a "free standing," monovalent (or "univalent") entity.

Persons of skill will appreciate that the dissociation constant ("Kd") of an antibody or other ligand is determined both by the $k_{on}$ and by the $k_{off}$ of the ligand. That is, the Kd represents the balance between the time the antibody or other ligand is bound to the target molecule and the time that it is not. A low affinity binding domain therefore often has a low affinity precisely because it has a high tendency to dissociate from its target molecule. During the period a binding domain dissociates from its target molecule, it can be moved away by Brownian movement, fluid flow, or other kinetic forces acting on the binding domain molecule. The tethering of the low affinity domain by the high affinity domain of the bsBA aids in maintaining the low affinity binding domain in proximity to the receptor targeted by the low affinity domain, and thus tends to increase the probability that at any point in time the low affinity domain will be able to bind its target molecule. Since the target molecule of the low affinity domain of the bsBAs of the invention in this hypothetical is a receptor kinase, this tends to increase the ability of the bsBA to bind the target receptor kinase and therefore increases their biological effect on target cells.

In preferred embodiments, the two binding domains of the bsBAs of the invention bind target molecules that are not normally bound by the same ligand. Persons of skill are aware that some ligands, such as the interleukin IL-2, for example, are bound by two different receptor chains, and that the two chains—with bound IL-2—then interact to form the fully biologically active unit. While bsBAs directed to the two receptor chains can therefore prevent full activation of such a receptor, both of the binding domains of such bsBAs are, of course, directed to the same receptor.

Finally, the formation of the trimer between the bsBA and the two target molecules bound by the binding domains has the additional advantage of binding the target molecules in close vicinity to one another and preventing their normal diffusion through the lipid bilayer of the cell membrane. The crosslinking of different receptors by bsBAs is itself believed to contribute to cytotoxic or cytostatic effects of the bsBAs on target cells. For example, signal transduction cascades typically are activated either by two proteins binding to each other to form a heterodimer or by a kinase that modifies (usually by phosphorylating) the next protein in the initiation cascade. Crosslinking of different receptors can interfere with the ability of the receptors to form their normal heterodimers or to modify the protein that would normally be the next step in the initiation cascade.

In one group of embodiments, the targeting domain of the bsBA binds to a cell surface receptor that is preferentially expressed or overexpressed on a target cell that is associated with a disease or disorder (for example, a breast cancer cell) and the effector domain binds to a cell surface receptor that is promiscuously or ubiquitously expressed on target cells and on non-target cells. Exemplar cell surface receptors that can be targeted by the bsBA of the invention are described below. In preferred embodiments, the molecule to be bound by the targeting domain is expressed on target cells at levels that are higher than the levels of the molecule to be bound by the effector domain. Thus, the bsBAs and methods of the invention are particularly useful for improving the specific delivery of effector molecules to cells with target molecules that would be promiscuously bound by conventional antibodies or bispecific, agents or by both. Persons of skill are aware that cells of different cancers may overexpress different antigens or may overexpress the same antigen to different degrees than do cells of a different cancer type. Thus, in designing the bsBAs of the invention, it is contemplated that the practitioner will select a targeting domain that targets a cell surface receptor overexpressed on the particular cells to be targeted by the particular bsBA.

In some embodiments, the targeting domain of the bsBA binds to a first cell surface receptor that is preferentially expressed or overexpressed on a target cell that is associated with a disease or disorder (for example, a cancer cell) and the effector domain binds to a second cell surface receptor that is overexpressed on disease cells (such as cancer cells) compared to normal cells, but is expressed at lower levels than is the first cell surface receptor. In these embodiments, the differential in expression level between the first and the second cell surface receptors again improves the specific delivery of effector molecules to cells with target molecules.

As noted in the Background, even though HER2 is overexpressed in breast cancer cells at levels some 10 to 100 times that of its expression on normal cells, some adverse side effects are seen in patients from binding of the immunotherapeutic agent, HERCEPTIN®, to normal cells. Thus, even substantial overexpression of a target molecule is not necessarily sufficient to keep high affinity binding agents from binding to normal cells, with adverse side effects.

By contrast, the bsBAs of the invention have a targeting domain that is chosen to have an affinity for its target molecule that is at least 10 times higher, and often much higher, than that of the effector domain. Preferably, the dissociation constant of the targeting domain for its target molecule is in the range of $10^{-8}$ to $10^{-12}$ M. The target molecule is selected either because it is not present on normal cells, or because it is highly overexpressed on cancer cells than on normal cells, preferably at least 20 times and even more preferably 100 times more than it is expressed on normal cells. As noted, due to the high affinity of the targeting domain for the target molecule, it will tend to bind the bsBA preferentially to the target cell. Thus, it is anticipated that the effector domain can target a target molecule expressed on normal cells and still achieve selective binding that provides a therapeutic window larger than that of conventional bsBAs.

Persons of skill will appreciate that cancer cells, in particular, tend to upregulate the expression of many normal proteins, including many with roles in maintaining homeostasis in normal cells. Thus, even proteins not normally considered to be cancer or tumor antigens tend to be upregulated on cancer cells. For instance, insulin receptor, which is not considered a tumor antigen, is often upregulated 3-5 fold on tumor cells as compared to normal cells (see, e.g., Milazzo et al., Cancer Res. 52 (14):3924-30 (1992)).

As another example, the ErbB3 receptor is somewhat overexpressed on some cancer cells compared to its expression on normal cells. It can, however, be used as the effector target molecule of a bsBA when the targeting domain is directed to a target molecule that is even more highly overexpressed. The Examples present an exemplar bsBA of the invention in which the targeting domain is directed to EGFR and the effector domain is targeted to ErbB 3.

It is desirable that the targeting domain is directed to a target molecule (such as a cancer antigen) that is overexpressed on the target cells, while the effector domain is directed to a molecule (e.g., a receptor kinase) that is expressed at a lower level than is the target molecule for the targeting domain. While it is only necessary that the target molecule is expressed at higher levels than the molecule targeted by the effector domain, in general, significant differences between the expression of the target molecule and the expression of the effector molecule are advantageous, since the effector molecules can be saturated at bsBA concentrations that are below the Kd of the targeting domain.

In general, it is preferable that the target molecule for the targeting domain is overexpressed at levels 10, 20, 50, 100, or more times higher than expression of that molecule on non-target cells, with each successively higher level being more preferred. In general, it is further preferred that the effector molecule be expressed either at the level it is expressed on non-target cells or, if it is overexpressed, that it is overexpressed at levels of 2 to 5 times that of non-target cells. In other words, it is preferable that the targeting molecule be expressed (or overexpressed) at high levels relative to the molecule bound by the effector domain.

Where the target cell is a disease cell, such as a cancer cell, the expression level of the target molecule is measured against the expression of the same molecule on normal cells of the same tissue type as that from which the cancer cell originates. That is, if the disease cell is a breast cancer cell, the expression level is measured against a normal breast cell, while the expression level of molecules of an ovarian cancer cell is measured against expression levels on normal ovary cells. Usually, a population of cells is used and an average value of expression level (e.g., number of molecules expressed per cell) is determined.

Further, in some preferred embodiments, the cell surface antigen recognized and bound by the effector domain is chosen to have a biological activity that can be modulated by the binding of the domain. For example, the cell surface antigen targeted by the effector domain can be a cytokine or growth factor receptor, the blockage of which by the domain will contribute to restoration of the target cell to a normal phenotype. It is expected that the blocking of the receptor will result in downregulating the pathway activated by the receptors, decreasing the rate of proliferation of the cell.

As noted above, antibodies are also known which can act as agonists of cytokine receptors and the like; that is, they act to enhance the activity of the target molecule. Thus, depending on the target molecules and binding agents selected by the practitioner, the effector domain of a bsBA of the invention may inhibit the activity of a target molecule, or may enhance it. The ability to select binding domains that increase or decrease the activity of the target molecule of the effector domain affords the practitioner considerable flexibility in designing bsBAs effective for a range of conditions. To indicate that the activities of the target molecule can be enhanced or decreased, at the practitioner's option, by the judicious selection of binding agent, the effect of the bsBAs on the target molecule is sometimes referred to herein as "modulating" the activity of the target molecule.

For example, some cancers result from the mutation of a gene encoding a receptor that acts as a tyrosine kinase, resulting in the receptor becoming either constitutively active or overexpressed, so that the cell proliferates more than it would with a normal receptor or with one expressed in normal amounts. To decrease the activity of the receptor, the practitioner may, in this example, select a binding agent whose binding is known to change the conformation of the constitutively active receptor to reduce its activity or, in the case of an overexpressed receptor, to simply block it from being bound by its natural ligand, thus preventing the overexpression from resulting in an inappropriate increase in signaling within the target cell. Conversely, if the target molecule is one whose activity it is desirable to enhance, the practitioner may select a binding agent whose binding is known to act as an agonist of the activity.

The use of bsBAs with a single high affinity binding domain is sufficient to provide specific binding to cells of interest. Studies have shown that binding agents with two high affinity binding domains directed to a single target molecule have only about three fold the affinity for the target molecule compared to a univalent binding agent with the same binding domain. Nielsen, U. et al., Cancer Res. 60 (22):6434-40 (2000). A univalent binding agent will therefore typically still have a Kd in the nanomolar range. Since therapeutic agents are typically administered in amounts to provide up to micromolar concentrations, a thousand times the Kd of the binding agent, the high concentration of the binding agent relative to the Kd of the high affinity targeting domain is expected to permit binding of the agent to target cells bearing the target molecule. Thus, the high affinity targeting domain of the bsBAs of the invention is expected to provide specific binding of the bsBAs under the conditions in which they will be administered.

It is expected that the practitioner can select appropriate combinations of target molecules for the targeting domain and for the effector domain. While a number of preferred target molecules and effector target molecules are described below, it may be helpful to list some preferred target molecules and effector target molecules. Some preferred target molecules are EGFR and ErbB2. Some preferred effector target molecules are: ErbB3, ErbB4, any of fibroblast growth factor (FGF) receptors 1-4, hepatocyte growth factor receptor, insulin-like growth factor 1 receptor (IGF1-R), insulin receptor, Platelet Derived Growth Factor (PDGF) receptors alpha and beta, and C-KIT. Each of these molecules is known in the art and is identified by its reference number in the SWISS-PROT database in a later section.

Finally, the bsBAs of the invention do not include bsBAs that bind HER3 with one binding domain and that bind HER2/neu with a second binding domain.

DEFINITIONS

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

"Affinity" of binding agents is typically stated in terms of their dissociation constant, or "$K_d$". Typically, useful binding agents have $K_d$s stated in nanomolar concentrations. Persons of skill will recognize that an antibody with a $K_d$ of $10^{-8}$ M has an affinity 10 times as high as one with a $K_d$ of $10^{-7}$, and 100 times the affinity of an antibody with a $K_d$ of $10^{-6}$. Thus, a higher affinity agent has a $K_d$ stated as a lower number (that is, $10^{-8}$ is a smaller number than is $10^{-6}$).

For convenience of reference, as used herein, the term "antibody" includes whole antibodies, antibody fragments that retain antigen recognition and binding capability, whether produced by the modification of whole antibodies or synthesized de novo using recombinant DNA methodologies, monoclonal antibodies, polyclonal antibodies, and antibody mimics, unless otherwise required by context. The antibody may be an IgM, IgG (e.g. $IgG_1$, $IgG_2$, $IgG_3$ or $IgG_4$), IgD, IgA or IgE.

The term "antibody fragments" means molecules that comprise a portion of an intact antibody, generally the antigen binding or variable region of the intact antibody. Examples of antibody fragments include Fab, Fab', F(ab')$_2$, and Fv fragments; helix-stabilized antibodies (see, e.g., Arndt et al., J Mol Biol 312:221-228 (2001); diabodies (see below); single chain Fvs ("scFvs," see, e.g., U.S. Pat. No. 5,888,773); disulfide stabilized antibodies ("dsFvs", see, e.g., U.S. Pat. No. 5,747,654), and domain antibodies ("dAbs," see, e.g., Holt et al., Trends Biotech 21 (11):484-490 (2003), Ghahroudi et al., FEBS Lett. 414:521-526 (1997), Lauwereys et al., EMBO J 17:3512-3520 (1998), Reiter et al., J. Mol. Biol. 290:685-698 (1999), Davies and Riechmann, Biotechnology, 13:475-479 (2001)).

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. See, Kabat and Wu, infra. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "$V_L$" refer to the variable region of an immunoglobulin heavy chain, including an Fv, scFv, dAb, dsFv or Fab. References to "$V_L$" or a "$V_L$" refer to the variable region of an immunoglobulin light chain, including of an Fv, scFv, dsFv, dAb, or Fab.

The phrase "single chain Fv" or "scFv" refers to an antibody in which the variable domains of the heavy chain and of the light chain of a traditional two chain antibody have been joined to form one chain. Optionally, a linker (usually a peptide) is inserted between the two chains to allow for proper folding and creation of an active binding site.

"Bispecific binding agents", or "bsBA," are binding molecules that are capable of specific binding to more than one type of target molecule simultaneously.

A "binding agent" is any molecule capable of specifically binding a target molecule and includes antibodies, antibody fragments, aptamers, peptides (e.g., Williams et al., J Biol Chem 266:5182-5190 (1991)), and antibody mimics, such as those that can be created from the tenth fibronectin type III domain (see, e.g., Xu, L., et al., Chem. Biol. 9 (8):933-42 (2002), Koide et al., J Mol Biol 284:1141-1151, Skerra, J Mol Recognit 13:167-187 (2000), Main et al., Cell, 71:671-678 (1992), and Dickinson et al., J Mol Biol, 236:1079-1092 (1994)), and can comprise natural proteins and proteins modified or engineered to include non-natural residues. In some embodiments, "binding agent" can also refer to the natural ligand for a receptor. For example, IL-13 can be used as a binding agent for the IL-13 receptor.

"Aptamer" refers in general to either an oligonucleotide of a single defined sequence or a mixture of said oligonucleotides, wherein the mixture retains the properties of binding specifically to the target molecule. Thus, as used herein "aptamer" denotes both singular and plural sequences of oligonucleotides. Structurally, the aptamers of the invention are specifically binding oligonucleotides. Oligonucleotides include not only those with conventional bases, sugar residues and internucleotide linkages, but also those which contain modifications of any or all of these three moieties. U.S. Pat. No. 5,756,291, incorporated herein by reference, provides a description of aptamers, methods of preparing and testing aptamers, and uses thereof.

"Target molecule" is used herein to refer to a molecule specifically bound by a binding domain of a bispecific binding agent of the invention. The terms "first target molecule" and "second target molecule" are used herein to refer to molecules of two distinct molecular species, rather than two molecules of the same molecular species. Such molecular species may be, for example, two different receptor tyrosine kinases (such as the basic fibroblast growth factor receptor 1 and the hepatocyte growth factor receptor). Some cytokine receptors and other receptors are composed of subunits known as "chains", and the receptor in some cases becomes fully activated by recruiting chains once the ligand for the receptor binds to one of the chains. As used herein, all the chains of a particular receptor (e.g., the IL-2 receptor) are considered to be of the same molecular species; therefore, if a chain of a given receptor is to be the "first target molecule" to be bound by a first binding domain of a bsBA of the invention, the "second target molecule" cannot be a second chain of the same receptor.

As used herein, "biological activity" refers to a defined, known activity performed by a target molecule. Most commonly, the biological activity of the molecules targeted by the bsBAs of the invention is signal transduction. For example, a later section of this specification lists a number of growth factor receptors as molecules that can be target molecules. These receptors typically have a ligand binding domain on the extracellular surface of the cell, a transmembrane domain, and a cytosolic domain which has tyrosine kinase enzyme activity. Typically, the tyrosine kinase activity is activated by the binding of a ligand to the ligand binding domain. The receptor kinase activity then initiates a signal cascade. Thus, the biological activity of these target molecules is signal transduction. Persons of skill will appreciate that the biological activity of a target molecule ultimately has an effect on the cell in which the target molecule is located. For example, the signal transduction cascade initiated by activating a growth factor receptor in a cancer cell overexpressing that receptor is likely to increase the growth and proliferation of the cell, while inhibiting the activity of the receptor is likely to inhibit or slow that proliferation. Thus, the term "biological activity" may also be used herein more broadly in connection with an activity of a cell in contrast to the activity of a target molecule. Which meaning is intended will be clear in context.

As stated above, some molecules that can be used as target molecules for bsBAs of the invention are not known to have a biological activity. Determining whether any given molecule on a cell surface does or does not have a biological activity for purposes of the present invention can be performed by the following means. A culture of human cells bearing the cell surface molecule can be divided to form two separate cultures. The first culture is contacted with a binding domain that specifically binds to the cell surface molecule and that is expected to block binding of any natural ligand for the molecule. The other group is not. The two groups are then cultured under otherwise identical conditions. For purposes of the present invention, the target molecule is considered not to have a "biological activity" if the binding of the molecule by the binding agent does not evoke an observable difference in cell proliferation, cell viability, apoptosis, activation of downstream kinases, transcriptional activation, adhesion to surfaces, or ability to grow colonies in soft agar. Assays for observing differences in these characteristics are well known in the art, and several are discussed in more detail below.

As used herein, "modulation" of a biological activity refers to increasing or inhibiting the biological activity of a target molecule, as the practitioner desires. For example, if the target molecule is a receptor considered to increase the proliferation of cancer cells (e.g., an ErbB3 receptor), the practitioner may desire to inhibit the receptor's activity by using a binding domain to bind to the receptor, blocking binding of the receptor by a natural ligand of the receptor. Frequently, these target molecules are receptors that act as tyrosine kinases upon binding of a natural ligand. Conversely, if the biological activity of the target molecule is one that the practitioner wishes to increase, the practitioner can, for example, use as the binding domain an antibody known in the art to act as an agonist of the target molecule. The result is intended to be beneficial to a disease or disease state being treated; e.g. for the treatment of malignancies and some autoimmune disorders, the desired effect would usually be inhibition of cell growth or the induction of apoptosis, or it could be the induction of the proliferation of a certain cell type, e.g. T-regulatory T-cells for the treatment of autoimmune disease.

It is understood that cell surface receptors have ligands that specifically bind to those receptors. With respect to a given receptor, therefore, the term "natural ligand" refers to a molecule that binds to that receptor in the course of normal physiology. For example, interleukin ("IL")-13 is the natural ligand for the IL-13 receptor, IL-2 is the natural ligand for the IL-2 receptor, epidermal growth factor is a natural ligand for the EGF receptor, and so on.

The terms "effective amount" or "amount effective to" or "therapeutically effective amount" includes reference to a dosage of an agent sufficient to produce a desired result, such as inhibiting cell protein synthesis by at least 50%, or killing the cell.

"Effector molecules" are defined as cell surface receptors which may be used to modulate the behavior of a cell, e.g. by signaling, phosphorylation, inducing proliferation, or inducing cell death, when contacted by a binding molecule, such as the effector domain of a bsBA of the invention.

"Kd" is the ratio of the reverse and forward rate constants for a reaction of the type:

$$A+B=AB.$$

At equilibrium, the equilibrium constant (K) equals the product of the concentrations of reactants divided by the concentration of product and has dimensions of concentration.

$$Kd=(\text{concentration } A \times \text{concentration } B)/(\text{concentration } AB).$$

"Univalent binding agent" and "univalent binding composition" are defined as a binding molecule with a single domain for binding a cell surface marker, as opposed, for example, to an intact immunoglobulin G molecule, which has two binding domains. A univalent binding agent is typically an isolated fragment of one of the two binding domains that form a bi-specific antibody such as an scFv, Fab', single domain antibody, etc.

A "target cell" is a cell to which a bispecific antibody binding agent of the invention is intended to preferentially bind by virtue of its high affinity targeting domain.

The term "contacting" includes reference to placement in direct physical association.

Cells are generally understood in the art to be bounded by a plasma membrane (commonly referred to as the "cell membrane") comprising a lipid bilayer, in which various proteins, such as transporters, ion channels, and cytokine receptors, are situated. See, generally, Alberts et al., Molecular Biology of the Cell, Garland Publishing, Inc., New York (3rd Ed., 1994), Chapter 10. The cell membrane may be considered to have a surface facing on the cytosol, or the interior of the cell, and a surface facing on the exterior of the cell, or the extracellular space. Transmembrane proteins are often amphipathic, that is, they have regions that are hydrophobic and regions that are hydrophilic. Regions that pass through the membrane are hydrophobic and interact with the hydrophobic tails of the lipid molecules comprising the bilayer. Regions that are hydrophilic are exposed to water on either the cytosolic or the extracellular side of the membrane. The transmembrane domain of transmembrane proteins are either in an alpha helix or multiple beta strands. See, e.g., Lodish et al., Molecular Cell Biology, W.E. Freeman and Co., New York (4th Ed., 2000), at chapter 3.

By "cytokine" is meant a generic term for proteins released by one cell population which act on the same cell population (autocrine) or another cell population (paracrine) as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), luteinizing hormone (LH); hepatic growth factor; fibroblast growth factor; prolactin; placental lactogen; tumor necrosis factor-α and β; mullerian-inhibiting substance; mouse gonadotropin-associated peptide; inhibin; activin; vascular endothelial growth factor (VEGF); integrin; thrombopoietin (TPO); nerve growth factors such as NGF-β; platelet-derived growth factor (PDGF); transforming growth factors (TGFs) such as TGF-α and TGF-β; insulin-like growth factor (IGF), e.g., IGF-I and IGF-II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL9, IL-11, IL-12; and other polypeptide factors including LIF and kit ligand (KL, also known as steel factor).

Unless otherwise indicated, references herein to amino acid positions of antibody heavy or light chains refer to the numbering of the amino acids under the "Kabat and Wu"" system. See, Kabat, E., et al., Sequences of Proteins of Immunological Interest, U.S. Government Printing Office, NIH Publication No. 91-3242 (1991), which is hereby incorporated by reference (the Kabat and Wu database and numbering system are also referred to herein as the "Kabat" system and numbering). The Kabat and Wu database is the most widely used system in the art for numbering amino acid residues of antibodies and is now too large to be conveniently printed. It is now maintained as a subscription service online, which can be found by entering "http://" followed by "immuno.bme.nwu.edu/". The number accorded to a residue under the Kabat and Wu system does not necessarily correspond to the number that one might obtain for a residue in a given heavy or light chain by counting from the amino terminus of that chain.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass analogs of natural amino acids that can function in a similar manner as naturally occurring amino acids.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table A each contain amino acids that are conservative substitutions for one another:

TABLE A

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, Proteins, W.H. Freeman and Company, New York (1984).

The terms "selectively reactive" and "selectively binds" refer, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing the target antigen or marker as compared to a cell or tissue lacking that antigen or marker. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Coupling the bsBAs to Therapeutic Agents or Labels

While the binding of the bsBAs to their ligands itself is intended to modulate the biological activity of the target cell by, for example, blocking access of cytokines to their receptors, the effect of the bsBA on biological activity can be increased by coupling a therapeutic agent to the bsBA. In some embodiments, therefore, the bsBAs are derivatized to introduce functional groups permitting the attachment of a therapeutic agent. The bsBA can be derivatized to introduce, for example, side chains terminating in hydrazide, hydrazine, primary amine, or secondary amine groups. Therapeutic agents can be conjugated through, for example, a Schiffs base linkage, a hydrazone or acyl hydrazone bond or a hydrazide linker (see, e.g., U.S. Pat. Nos. 5,474,765 and 5,762,918, each of which is specifically incorporated herein by reference). A number of other chemistries suitable for conjugating therapeutic agents to bsABs of the invention are well known in the art, as exemplified by Hermanson, G., Bioconjugate Techniques, Academic Press, San Diego, Calif. (1996).

Therapeutic agents can be selected from, for example, anti-neoplastic agents, anti-metabolic agents, radioactive agents, cytotoxic agents, and chemotherapeutic agents.

Cytotoxic agents include anti-cancer agents, such as the following: gemcitabine; methotrexate; 5-FU; FUDR; FdUMP; hydroxyurea; docetaxel; discodermolide; epothilones; vincristine; vinblastine; vinorelbine; meta-pac; irinotecan; SN-38; 10-OH campto; topotecan; etoposide; adriamycin; flavopiridol; cisplatin; carboplatin; bleomycin; mitomycin C; mithraniycin; capecitabine; cytarabine; 2-Cl-2'deoxyadenosine; mitoxantrone; mitozolomide; pentostatin; and raltitrexed.

The bsBAs of the invention can further be modified or labeled to facilitate diagnostic or therapeutic uses. For example, detectable labels such as a radioactive, fluorescent, heavy metal, or other label, may be conjugated to the bsBAs of the invention. Single, dual, or multiple labeling of the bsBAs may be advantageous. For example, a bsBA can be dual labeled, with both radioactive iodination of one or more residues and the coupling of, for example, $^{90}$Y via a chelating group to amine-containing side or reactive groups. This combination labeling can be useful for specialized diagnostic needs such as identification of widely dispersed small neoplastic cell masses.

Radioisotopes for radiolabeling the bsBAs of the invention include any radioisotope that can be conjugated or coupled to a residue of the bsBAs. The radioisotopes can be selected from radioisotopes that emit either beta or gamma radiation, or alternatively, the peptide agents can be modified to contain chelating groups that, for example, can be covalently bonded to lysine residue(s) of the analog. The chelating groups can then be modified to contain any of a variety of radioisotopes, such as gallium, indium, technetium, ytterbium, rhenium, or thallium (e.g., $^{125}$I, $^{67}$Ga, $^{111}$In, $^{99}$mTc, $^{169}$Yb, $^{186}$Re).

Chelating groups may be used to indirectly couple detectable labels or other molecules to the bsBAs of the invention. For example, a bifunctional stable chelator may be linked to one or more terminal or internal amino acid reactive groups via an isothiocyanate beta-Ala or an appropriate non alpha-amino acid linker which prevents Edman degradation. Examples of chelators known in the art include, for example, the ininocarboxylic and polyaminopolycarboxylic reactive groups, DTPA (N,N-Bis[2-[bis(carboxymethyl)amino]ethyl] glycine), and DOTA (1,4,7,10-tetraazacyclododecane-1,4,7, 10-tetraacetic acid).

In terms of cancer diagnosis and treatment, the bsBAs of the invention can be used to prepare diagnostic and imaging compositions, and kits utilizing the bsBAs in diagnostic and imaging methods (e.g., in vivo and in vitro diagnostic methods). For example, a vascularized tumor may be imaged using a diagnostically effective amount of a bsBA that includes at least a first binding molecule that binds to an accessible component of a tumor cell, tumor vasculature, or tumor stroma, attached to an in vivo diagnostic imaging agent.

In another preferred embodiment in which the disease or disorder is cancer, pre-imaging before cancer treatment may be carried out by: (a) administering to the animal or patient a diagnostically effective amount of a pharmaceutical composition comprising a detectably-labeled bsBA of the invention that has a first binding molecule that binds with high affinity to a highly expressed receptor characteristic of a tumor cell, or to the tumor vasculature or tumor stroma, and a second binding molecule that binds with at least an order of magnitude lower affinity to a second ubiquitously-expressed receptor (e.g., ErbB3 or ErbB4); and (b) subsequently detecting the detectably-labeled bsBA bound to the tumor cells, tumor blood vessels, or tumor stroma; thereby obtaining an image of the tumor, tumor vasculature, and/or tumor stroma.

Without wishing to be bound by theory, the bsBA can reduce, prevent, or inhibit cell signaling by competing with a natural ligand for binding to a cell surface receptor. In this situation, the bsBA functions by blocking cell signaling induced upon ligand binding. The bsBA can also act by inducing internalization/downregulation of the cell surface receptors. The reduction in the number of receptors at the cell surface caused by internalization/downregulation results in reduced receptor activation, which reduces or prevents cell signaling along the signal transduction pathway for those receptors. Finally, in cases where receptor dimerization is required for signal transduction, the bsBA can act by preventing dimerization of the two cell surface receptors.

Selecting Cell Markers for Use as Targets and for Effectors

Cell markers used for targeting bsBAs typically are expressed at higher levels on the target cell than on non-target cells, or are not expressed on non-target cells. For example, a target marker may be highly overexpressed in particular cancers compared to its expression in non-target cells, or may not be expressed by cells that are not cancerous.

The cell markers used as effectors are typically involved in cellular signaling, such as growth factor, cytokine, or chemokine receptors, that are beneficial to modulate in given pathological conditions. Because of the selectivity provided by the hi-lo bsBAs of the invention, the expression of the marker bound by the bsBA effector domain need not be confined to the target cell and may be expressed on other cells of the organism.

Measuring Kd

The binding affinity of the binding molecules of the bsBA can be determined using methods known in the art, e.g., as described in U.S. Pat. No. 6,703,020, incorporated herein by reference. The binding affinity of the first and second binding molecules of the bsBA to their respective target receptors, and the off-rate of bsBA-receptor complexes, can be determined by competitive binding assays. One example of a competitive binding assay is a radioimmunoassay comprising incubating one or both receptors, labeled with, for example, $^3$H or $^{125}$I, with a bsBA of interest in the presence of increasing amounts of unlabeled receptor, and detecting bsBA bound to the labeled receptor. The affinity of the bsBA of interest for a particular receptor and the binding off-rates can be determined from the data by, for example, Scatchard plot analysis. The Kd may also be determined by flow cytometry as described, for example, in Nielsen et al. (Cancer Res. 60 (22):6434-40 (2000)). An exemplary assay for determining Kd is set forth in the Examples.

In preferred methods, the receptor-binding affinities of the bsAb is determined from association and dissociation rate constants measured using a BIAcore surface plasmon resonance system (BIAcore, Inc., Piscataway, N.J.). Typically, the affinity of the bsBA to the ligand molecule is determined by immobilizing an appropriate amount (e.g., 500 resonance units) on a biosensor chip (BIAcore). On- and off-rates of the bsBAs are typically measured in PBS by injecting 25 μg/ml of the bsBA over the chip surface for 5 minutes and then allowing the bound material to dissociate for 5 minutes by flowing the buffer solution over the chip. Binding kinetics can be analyzed using, for example, BIAevaluation 2.1 software (BIAcore). For purposes of determining whether a particular bsBA falls within the scope of this invention, the affinities of the binding domains of the bsBA are determined after the bsBA is formed (as opposed to measuring the affinity of the domains individually prior to their placement in the bsBA) so that the relative affinity of the binding domains can be determined.

Measuring Desired Biological Effects

The bsBAs of the invention are preferably first tested in vitro for the desired therapeutic or prophylactic activity. For example, in vitro assays that can be used to demonstrate the therapeutic or prophylactic utility of the bsBAs include the effect of a bsBA on a cell line or a patient tissue sample.

The effect of the bsBA on the cell line and/or tissue sample can be determined utilizing techniques known to those of skill in the art including, e.g., cell proliferation assays, cell viability assays, assays of protein phosphorylation, protein kinase activity, apoptosis assays, and protein synthesis inhibition studies, among others. Antibody microarrays can be used to determine the effect on multiple protein in a protein pathway. Such assays are described in, for example, Nielsen et al. (Proc Natl Acad Sci USA., 100 (16):9330-5. (2003)) ("Nielsen 2003"). The bsBAs are then tested in vivo for efficacy in non-human animals prior to commencing human clinical trials.

Creating Univalent Binding Compositions

When the bsBA is created by chemical cross linking, the non-cross-linked fragments are themselves univalent binding fragments. In the case of the genetically linked (that is, recombinantly expressed) bsBA's, the univalent binding compositions can be created by cloning the individual binding proteins into expression vectors that allow the expression and isolation of the monovalent binding protein. The affinity of the individual, univalent binding compositions can then be determined as set forth above.

Testing for Equivalent $K_d$

Equivalent $K_d$'s may be determined by the methods set forth above, using the univalent binding compositions.

Comparing the Binding of bsBAs and Univalent Binding Compositions

The univalent binding compositions and the bsBA may be subjected to biological activity assays, e.g., in order to evaluate its effectiveness as a therapeutic and to compare the effectiveness of the bsBA. Such assays are known in the art and depend on the target antigen. Examples include the measurement of AKT phosphorylation by ELISA or immunoblotting following activation with heregulin or other growth factors, growth inhibition assays (as described for example, in WO 89/06692); or assays of apoptosis.

For phosphorylation, standard immunoblotting may be used to determine the effect of the binding molecules on e.g. activation of the effector molecule itself or downstream kinases or antibody arrays may be employed as is described in detail in Nielsen 2003, supra.

For apoptosis, DNA fragmentation can be detected in vitro using standard electrophoresis or TUNEL (terminal deoxynucleotidyl transferase dUTP nick end labeling) assays that detect DNA nicks in apoptotic cells. Once the cells are fixed, DNA strand breaks can be detected in situ using mammalian terminal deoxynucleotidyl transferase (TdT), which covalently adds labeled nucleotides to the 3'-hydroxyl ends of these DNA fragments in a template-independent fashion.

Cell viability and proliferation can be monitored with various chemical and biological reagents. For example, antibodies to cell-cycle-related markers or fluorescence-based cell viability and proliferation assays such as tritiated thymidine assays, trypan blue exclusion assays, the ATCC Bioproducts™ MTT Cell Proliferation Assay (American Type Culture Collection, Manassas, Va.), or the CellTiter-Blue® Cell Viability Assay (Promega, Madison, Wis.).

Use of bsBAs to Bind Growth Factor Receptors

A number of molecules can be bound by the effector domain of a bsBA of the invention. In one important series of embodiments, the effector domain binds a growth factor receptor on a cell surface, such as a tyrosine kinase receptor. The overexpression or inappropriate activation of a number of important growth factor receptors and their ligands, such as those belonging to the epidermal growth factor (EGF), fibroblast growth factor (FGF), insulin-like growth factor (IGF-1), platelet-derived growth factor (PDGF), and vascular endothelial growth factor (VEGF) families are known to be associated with or responsible for the initiation and progression of diseases and disorders, such as cancer and autoimmune diseases. It is thought that these growth factors act in an autocrine and/or paracrine manner to stimulate survival, proliferation, or migration of diseased cells. Binding of growth factors to their receptors results in activation of the receptor, e.g., by receptor dimerization, which results in receptor autophosphorylation and subsequent signal transduction via an array of different signaling molecules.

Interfering with the activity of the binding of the growth factor or activation of the tyrosine kinase receptors in such cells can restore a non-cancerous phenotype or reduce the rate of proliferation of affected cells. That is, contacting the receptor with a bsBA of the invention blocks the signals generated upon the binding of ligands, e.g., growth factors, to their cell surface receptors. The bsBA prevents or reduces activation of the signal transduction pathway by preventing or reducing ligand binding to the receptor, or by preventing or reducing ligand-induced receptor dimerization.

Exemplar tyrosine kinase receptors (with alternative names shown in parentheses) that can be bound by the effector domain of the bsBA to effect a useful result in the methods of the invention include:

ALK (anaplastic lymphoma kinase), a tyrosine kinase receptor expressed as part of the chimeric NPM-ALK protein, in anaplastic large cell lymphomas (ALCLs);

Discoidin domain receptor (DDR), a receptor tyrosine kinase that is distinguished by a unique extracellular domain homologous to the lectin Discoidin I (Discoidin receptor tyrosine kinase) (Tyrosine-protein kinase CAK) (Cell adhesion kinase) (TRK E) (Protein-tyrosine kinase RTK 6) (CD167a antigen);

Discoidin domain receptor 2 precursor (Receptor protein-tyrosine kinase TKT) (Tyrosine-protein kinase TYRO 10) Neurotrophic tyrosine kinase, receptor-related 3);

Epidermal growth factor receptor (Receptor protein-tyrosine kinase ErbB-1);

Receptor protein-tyrosine kinase erbB-2 (p185erbB2) (NEU proto-oncogene) (C-erbB-2);

Receptor protein-tyrosine kinase erbB-3 precursor (c-erbB3) (Tyrosine kinase-type cell surface receptor);

Receptor protein-tyrosine kinase erbB4 (p180erbB4) (Tyrosine kinase-type cell surface receptor);

Basic fibroblast growth factor receptor 1 (FGFR-1) (bFGF-R) (Fms-like tyrosine kinase-2) (c-fgr);

FL cytokine receptor (Tyrosine-protein kinase receptor FLT3) (Stem cell tyrosine kinase 1) (STK-1) (CD135 antigen);

Mast/stem cell growth factor receptor (SCFR) (Proto-oncogene tyrosine-protein kinase Kit) (c-kit) (CD117 antigen);

Leukocyte tyrosine kinase receptor (Protein tyrosine kinase-1);

Hepatocyte growth factor receptor (Met proto-oncogene tyrosine kinase) (c-met) (HGF receptor) (HGF-SF receptor);

Protein-tyrosine phosphatase eta (R-PTP-eta) (HPTP eta) (Protein-tyrosine phosphatase receptor type J) (Density enhanced phosphatase-1) (DEP-1) (CD148 antigen);

Proto-oncogene tyrosine-protein kinase receptor ret (C-ret);

Tyrosine-protein kinase transmembrane receptor ROR1 (Neurotrophic tyrosine kinase, receptor-related 1);

Tyrosine-protein kinase transmembrane receptor ROR2 (Neurotrophic tyrosine kinase, receptor-related 2);

Tyrosine-protein kinase receptor Tie-1;

Angiopoietin 1 receptor (Tyrosine-protein kinase receptor TIE-2) (Tyrosine-protein kinase receptor TEK) (P140 TEK) (Tunica interna endothelial cell kinase) (CD202b antigen);

High affinity nerve growth factor receptor (TRK1 transforming tyrosine kinase protein) (p140-TrkA) (Trk-A);

BDNF/NT-3 growth factors receptor (TrkB tyrosine kinase) (GP145-TrkB) (Trk-B);

NT-3 growth factor receptor (TrkC tyrosine kinase) (GP145-TrkC) (Trk-C);

Vascular endothelial growth factor receptor 1 (VEGFR-1) (Vascular permeability factor receptor) (Tyrosine-protein kinase receptor FLT) (Flt-1) (Tyrosine-protein kinase FRT) (Fms-like tyrosine kinase 1);

Vascular endothelial growth factor receptor 2 (VEGFR-2) (Kinase insert domain receptor) (Protein-tyrosine kinase receptor Flk-1); and Vascular endothelial growth factor receptor 3 precursor (EC 2.7.1.112) (VEGFR-3) (Tyrosine-protein kinase receptor FLT4).

The discussion below describes more specific information about tyrosine kinase receptors that are particularly useful to bind with an effector domain, as well as other receptor families that can usefully be regulated by the methods of the invention.

Epidermal Growth Factor Receptor (EGFR)/ErbB Receptor

The EGFR/ErbB family of single-spanning, tyrosine kinase receptors consists of four members: epidermal growth factor receptor (EGFR), ErbB2 (HER2/neu), ErbB3 (HER3) and ErbB4 (HER4). A number of ligands, all of which are different gene products, have been identified that bind and activate the ErbB receptors. These receptors and ligands play key roles in normal cell growth and differentiation.

Aberrant signaling and/or unregulated activation of ErbB receptor proteins has been linked to the development and progression of many cancers. Uncontrolled cellular proliferation mediated via dysfunctional ErbB receptor pathways can be found in a wide variety of solid cancers of epithelial origin and data have linked tumor ErbB receptor expression, overexpression and/or dysregulation to advanced disease, metastatic phenotype, resistance to chemotherapy and an overall poorer prognosis. Furthermore, data has also implicated ErbB receptors in increased tumor invasion, inhibition of cellular apoptosis, increased cellular adhesion and angiogenesis. In particular, increased expression of the EGFR has been observed in more aggressive carcinomas of the breast, bladder, lung and stomach (Modjtahedi and Dean, Int. J. Oncol. 4:277-296, (1994)). Overexpression of human ErbB2 has been associated with breast and ovarian cancers (Slamon et al., Science 235:177-182 (1987) and Slamon et al., Science 244:707-712 (1989)), and carcinomas of the stomach, endometrium, salivary gland, lung, kidney, colon and bladder. Markedly elevated levels of ErbB3 have been associated with certain human mammary tumor cell lines indicating that ErbB3, like ErbB1 and ErbB2, plays a role in human malignancies. Specifically, ErbB3 has been found to be overexpressed in breast (Lemoine et al., Br. J. Cancer 66:1116-1121, 1992), gastrointestinal (Poller et al., J. Pathol. 168:275-280, 1992; Rajkumer et al., J. Pathol. 170:271-278, 1993; and Sanidas et al., Int. J. Cancer 54:935-940, 1993), and pancreatic cancers (Lemoine et al., J. Pathol. 168:269-273, 1992, and Friess et al., Clinical Cancer Research 1:1413-1420, 1995). Finally, increased ErbB4 expression is also closely correlated with human carcinomas, e.g., carcinomas of epithelial origin, including breast adenocarcinomas.

Signal transduction mediated by the ErbB family of protein receptors occurs, in many instances, upon ligand-induced receptor heterodimerization. "Receptor cross-talking" following heterodimerization results in activation of the ErbB receptor kinase domain and cross-phosphorylation of the ErbB receptors, which is known to occur between, e.g., EGFR and ErbB2, ErbB2 and ErbB3, and ErbB2 and ErbB4 (see, e.g., Wada et al., Cell 61:1339-1347 (1990); Plowman et al., Nature 336:473-475 (1993); Carraway and Cantley, Cell 78:5-8 (1994); Riese et al., Oncogene 12:345-353 (1996); Kokai et al., Cell 58:287-292 (1989); Stern et al., EMBO J. 7:995-1001 (1988); and King et al., Oncogene 4:13-18 (1989)).

Preferred binding molecules for use in preparing the bsBAs of the invention are described in, e.g., U.S. Pat. Nos. 5,183,884, 5,480,968, 5,968,511, 5,977,322, and 6,512,097; Kraus et al., Proc. Natl. Acad. Sci. USA 86:9193-9197 (1989); European Pat. Appln. No. 444,961A1; and Kraus et al., Proc. Natl. Acad. Sci. USA 90:2900-2904 (1993), each of which is incorporated herein by reference. Embodiments of the method of treatment encompass a disease state or states in addition to cancer, such as immunological disorders, neurological disorders, such as neurofibromatosis and peripheral neuropathy, and cardiac disorders, such as cardiac hypertrophy.

Insulin Receptor (IR) and Insulin-Like Growth Factor Receptor (IGF-R)

The insulin receptor and IGF-1 receptors are closely related proteins that are important targets for the development of new therapeutics for two major diseases, diabetes and cancer. Diabetes is a global health problem of increasing importance. It is the only non-infectious disease classified by the World Health Organization as an epidemic. Worldwide the incidence of diabetes is 2-3%, rising to 6% in the USA and other Western countries.

There is growing evidence that the insulin-like growth factor receptors (IGFRs) play an important role in certain cancers and psoriasis. Deregulated signaling by these receptors is associated with the pathogenesis of, e.g., Wihn's tumorigenesis, hepatoblastoma, hepatocarcinoma, colorectal cancer, breast cancer, adrenocortical carcinoma, multiple myeloma, lymphoma, leukemia, prostate cancer, and lung cancer, with resistance to radiotherapy and chemotherapy. The insulin and IGF receptors are closely related to the ErbB receptor family.

The insulin-like growth factor receptors (IGFRs) are involved in the maintenance of normal function of many cells of the body. IGF-II receptor is commonly expressed by tumor cells and may act as an autocrine growth factor; occasionally even reaching target tissues and causing tumor-induced hypoglycemia. IGF-I receptor is commonly overexpressed in many cancers, and many recent studies have identified new signaling pathways emanating from the IGF-I receptor that affect cancer cell proliferation, adhesion, migration, and cell death; functions that are critical for cancer cell survival and metastases (see, e.g., LeRoith et al., Cancer Lett. 195:127-137 (2003)). The IGF-I receptor has not been viewed as a likely target for cancer therapeutics because many normal cells also express this receptor. Scientific evidence suggests that IGF-I receptor inhibition impacts multiple intracellular signals related to cell proliferation or tumor development and provides possible mechanisms to explain how IGF-I receptor inhibition can make tumor cells more sensitive to conventional chemotherapy or other anticancer agents. Perhaps most significantly, inhibiting the signaling of IGF-I receptor suppresses tumor growth, prolongs patient survival, and enhances the antitumor effect of chemotherapy in clinically relevant mouse models of multiple myeloma and other hematological malignancies. Therefore, it is envisioned that a bsBA in which the low affinity binding molecule of the bsBA binds to the IGF-I receptor will overcome the deficiencies of the prior art therapeutics that preferentially target the IGF-I receptor (i.e., by avoiding the inhibition of IGF-I receptor signaling in non-target, non-diseased cells). In this instance, it is preferable that the high affinity binding molecule of the bsBA binds to a cell surface receptor that specifically targets the bsBA to the diseased cells (e.g., cells in which inhibition of overstimulation of the IGF-I receptor is desired). Once preferentially targeted to diseased cells, the low affinity binding molecule of the bsBA can then bind to IGF-I and inhibit the inappropriate cell signaling associated with the disease state.

Therapeutic strategies for patients with advanced-stage adenocarcinoma of the breast frequently include the use of cytotoxic chemotherapy. IGF-I receptor, a key factor in cell-cycle regulation, is frequently overexpressed in high-grade breast cancers and represents a primary target in these cancers. It has also been noted that patients being treated for breast cancer using an anti-HER2/neu receptor monoclonal antibody (Trastuzumab, also known as Herceptin®), which inhibits growth of ErbB2-overexpressing breast cancer cells, commonly develop resistance to the antibody. It has been observed that insulin-like growth factor-I (IGF-I), which activates cell survival signals, interferes with the growth-inhibitory action of trastuzumab. By preventing, reducing, or inhibiting cell signaling through the IGF-I receptor using a bsBA of the invention, trastuzumab-induced growth inhibition can be restored (see, e.g., Lu et al., J. Natl. Cancer Inst. 93:1852-1857, 2001). Thus, one possible use of the bsBA of the invention is to target IGF-I receptor signaling to prevent or delay development of resistance to trastuzumab or other current or future anti-cancer therapeutics.

Central nervous system (CNS) atypical teratoid/rhabdoid tumors (ATT/RhT) are among the pediatric malignant tumors with the worst prognosis and fatal outcome. To date there are no explanations for their remarkable resistance to cytostatic drugs and radiotherapy. IGF-I receptor plays a critical role in cell survival, proliferation, transformation, and regulation of apoptosis. IGF-I receptor protects cancer cells from apoptosis induced by a variety of anticancer drugs and radiation, but when impaired by inhibitors such as antisense strategies, dominant negative mutants, or triple-helix formation, tumor cells undergo massive apoptosis, resulting in an inhibition of tumorigenesis and metastases in experimental animal models. A bsBA of the invention that targets the IGF-I receptor can be used to prevent or reduce the signal transduction via activation of the IGF-I receptor, and thereby treat the disease conditions, such as cancer.

Cross-talk between insulin-like growth factor (IGF)- and estrogen receptor (ER)-signaling pathways results in synergistic growth. Estrogen enhances IGF signaling by inducing expression of IGF-I receptor and its downstream signaling molecules, and insulin receptor substrate (IRS)-1 and IRS-2. Estrogen induction of IGF-I receptor and IRS expression results in enhanced tyrosine phosphorylation of IRS-1 after IGF-I stimulation, followed by enhanced mitogen-activated protein kinase activation. This indicates that activation of the IGF-I receptor is involved in estrogen-mediated growth and breast cancer pathogenesis (see, e.g., Lee et al., Mol. Endocrinol. 13:787-796, 1999). Therefore, a bsBA of the invention that targets the IGF-I receptor can be used to prevent or reduce the signal transduction via activation of the IGF-I receptor, and thereby treat estrogen-induced breast cancer disease conditions.

Vascular Endothelial Growth Factor Receptor (VEGFR)

Vascular endothelial growth factor (VEGF) is a multifunctional cytokine that is induced by hypoxia and oncogenic mutations. VEGF is a primary stimulant of the development and maintenance of a vascular network in embryogenesis. It functions as a potent permeability-inducing agent, an endothelial cell chemotactic agent, an endothelial survival factor, and an endothelial cell proliferation factor (Thomas, J. Biol. Chem. 271:603-606, 1996; and Neufeld et al., FASEB J. 13:9-22, 1999). VEGF is an important factor driving angiogenesis or vasculogenesis in numerous physiological and pathological processes, including wound healing (Frank et al., 1995; Burke et al., 1995), diabetic retinopathy (Alon et al., 1995; Malecaze et al., 1994), psoriasis (Detmar et al., 1994), atherosclerosis (Inoue et al., 1998), rheumatoid arthritis (Harada et al., 1998; Nagashima et al., 1999), and solid tumor growth (Plate et al., 1994; Claffey et al., 1996).

A wide variety of cells and tissues produce VEGF. VEGF dimers bind with high affinity to two well-characterized receptors, VEGFR1 (FLT-1) and VEGFR2 (KDR/Flk-1), which are selectively expressed on endothelial cells (Flt-1 and Flk-1 are the mouse homologues). The Kd of VEGF binding to VEGFR1 and VEGFR2 is 15-100 pM and 400-800 pM, respectively (Terman et al., 1994). A recently identified third cell surface protein, neuropilin-1, also binds VEGF with high affinity (e.g., Soker et al., Cell. 92 (6):73545 (1998)).

VEGFR1 and VEGFR2 are members of the Type III receptor tyrosine kinase (RTK III) family that is characterized by seven extracellular IgG-like repeats, a single spanning transmembrane domain, and an intracellular split tyrosine kinase domain (Mustonen and Alitalo, J Cell Biol 129: 895-898 (1995)). Until very recently, VEGFR1 and VEGFR2 were thought to be almost exclusively expressed on endothelial cells (id.). Recent studies have shown that each of VEGF, VEGFR1, and VEGFR2 are essential for vasculogenesis, angiogenesis, and embryo development. VEGFR1 has a higher affinity for VEGF than VEGFR2, although it has a lower tyrosine kinase activity.

Binding of the VEGF dimer to the VEGF receptor is believed to induce receptor dimerization. Dimerization of the receptor then causes autotransphosphorylation of specific tyrosine residues, which leads to a signal transduction cascade. The intracellular events further downstream in VEGF-induced signaling are less clear, although a number of groups have shown that nitric oxide (NO) is produced after VEGF activation of VEGFR2 (Kroll and Waltenberger, Biochem Biophys Res Commun. 252 (3):743-6 (1998)). Activation of VEGFR2, but not VEGFR1, by VEGF has also been shown to activate Src and the Ras-MAP kinase cascade, including the MAP kinases, ERK 1 and 2 (Kroll and Waltenberger, J Biol Chem. 272 (51):32521-7 (1997)).

Preferred binding molecules for use in preparing the bsBA of the invention are described in, e.g., U.S. Pat. Nos. 5,840,301, 5,874,542, 6,703,020, and in WO 99/40118, each of which is incorporated herein by reference. A preferred binding molecule for use in preparing the bsBA is monoclonal antibody 2C3 (ATCC PTA 1595). RNA aptamers, antisense molecules and ribozymes against the VEGF receptors can also be used as a binding molecule in the bsBA. Preferred RNA antisense molecules, aptamers and ribozymes are described in, e.g., Saleh et al., Cancer Res. 56 (2):393-401 (1996); Cheng et al., Proc Natl Acad Sci USA. 93 (16):8502-7 (1996); Ke et al., Int J. Oncol. 12 (6):1391-6 (1998); and Parry et al., Nucleic Acids Res. 27 (13):2569-77. (1999); each of which is incorporated herein by reference.

The compositions and methods of use of the present invention are particularly intended for use in animals and patients (e.g., human patients) that have, or are at risk for developing, any form of vascularized tumor; macular degeneration, including age-related macular degeneration; arthritis, including rheumatoid arthritis; atherosclerosis and atherosclerotic plaques; diabetic retinopathy and other retinopathies; thyroid hyperplasias, including Grave's disease; hemangioma; neovascular glaucoma; and psoriasis, which are associated with inappropriate or excessive activation of a VEGF receptor.

The compositions and methods of use of the invention are further intended for the treatment of animals and patients that have, or are at risk for developing, arteriovenous malformations (AVM), meningioma, and vascular restenosis, including restenosis following angioplasty, conditions that are also associated with inappropriate or excessive activation of a VEGF receptor. Other intended targets of the therapeutic methods and uses are animals and patients that have, or are at risk for developing, the following VEGF receptor-related conditions: angiofibroma, dermatitis, endometriosis, hemophilic joints, hypertrophic scars, inflammatory diseases and disorders, pyogenic granuloma, scleroderma, synovitis, trachoma and vascular adhesions.

The treatment groups listed above are not exhaustive of the conditions that can be treated by the bsBAs of the invention. U.S. Pat. No. 5,712,291, incorporated herein by reference, discloses a method of identifying a number of other conditions that may be effectively treated by using the bsBA of the invention when the effector domain is directed to one of the VEGF receptors. Furthermore, additional conditions that can be treated using a bsBA of the invention that has the effector domain binding a VEGFR can be found in, e.g., U.S. Pat. No. 6,703,020, incorporated herein by reference.

Tumor Necrosis Factor Receptor (TNFR)

Tumor necrosis factors (TNF) alpha and beta are cytokines that act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized. Among the ligands there are included TNF-, lymphotoxin-(LT-, also known as TNF-β), LT-β (found in complex heterotrimer LT-2-β), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (see, e.g., A. Meager, Biologicals 22:291-295, 1994).

Many members of the TNF-ligand superfamily are expressed by activated T-cells, implying that they are necessary for T-cell interactions with other cell types which underlie cell ontogeny and functions. (Meager 1994, supra). Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (see, e.g., Watanabe-Fukunaga et al., Nature 356:314, 1992), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (see, e.g., R. C. Allen et al., Science 259:990, 1993). Targeted mutations of the low affinity nerve growth factor receptor cause a disorder characterized by faulty sensory innovation of peripheral structures (see, e.g., Lee et al., Cell 69:737, 1992).

The TNFR ligands, TNF and LT-, are capable of binding to two TNF receptors (the 55- and 75-kd TNF receptors). A large number of biological effects elicited by TNF and LT-, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT- are involved in the pathogenesis of a wide range of diseases, including endotoxic shock, cerebral malaria, tumors, autoimmune disease, AIDS and graft-host rejection (Beutler and Von Huffel, Science 264:667-668, 1994). Mutations in the p55 receptor cause increased susceptibility to microbial infection.

Another TNFR, TNF-related apoptosis-inducing ligand or "TRAIL," is expressed in many human tissues (e.g., spleen, lung, prostate, thymus, ovary, small intestine, colon, peripheral blood lymphocytes, placenta, kidney). It has been shown that TRAIL acts independently from the FAS ligand and activates apoptosis rapidly, within a time frame that is similar to death signaling by Fas/Apo-1L, but much faster than TNF-induced apoptosis.

Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes. Cellular response to TNF-family ligands include not only normal physiological responses, but also diseases associated with increased apoptosis or the inhibition of apoptosis. Apoptosis-programmed cell death is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft vs. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia, and anorexia.

The bsBA of the invention can be prepared so that at least one of the two binding domains specifically binds to a TNFR. Such a bsBA can then be used in methods for treating cancers, autoimmune disorders, viral infections, inflammation, graft vs. host disease, acute graft rejection, and chronic graft rejection by activating a TNFR, e.g., by binding the TNFR, thereby promoting apoptosis and preventing or reducing inappropriate cell growth (e.g., in cases of cancer). In a preferred embodiment, one of the binding molecules of the bsBA binds a TNFR and the second binding molecule binds to a second receptor that is known to be expressed on the target cell (e.g., a second, different TNFR, or a disease-specific receptor). In the case of cancer, a preferable second receptor is a receptor of the ErbB family, such as ErbB2. Preferably, the binding molecule of the bsBA that binds the TNFR has a lower affinity than the affinity that the second binding molecule has for its receptor.

Alternatively, the bsBA of the invention can be prepared so that at least one of the two binding molecules of the bsBA specifically binds to a TNFR and prevents or reduces activation of the TNFR, e.g., by blocking ligand binding to the TNFR. Such a bsBA can then be used in methods for treating AIDS, neurodegenerative disorders, myelodysplastic syndromes, ischemic injury, toxin-induced liver disease, septic shock, cachexia, and anorexia by preventing or reducing activation of a TNFR, e.g., by preventing or reducing ligand binding to the TNFR, thereby preventing or reducing apoptosis. Preferably, a bsBA in which at least one of the two binding molecules specifically binds to a TNFR is used to treat a disease wherein increased apoptosis is exhibited (e.g., ischemic injury). In a preferred embodiment, the targeting domain of the bsBA is directed to an antigen or a second receptor that is expressed on the target cell (i.e., a receptor other than the TNFR), which is used to target the bsBA to the target cell.

Fibroblast Growth Factor Receptor (FGFR)

The fibroblast growth factor (FGF) signaling pathway is an important part of normal development and wound healing. The FGFs produce their effects through cell surface receptors, which are members of the tyrosine kinase family. In humans, 4 different fibroblast growth factor receptors (FGFRs) have been identified (FGFR1-FGFR4).

The FGFRs are activated by autophosphorylation following dimerization. The dimerization occurs after ligand binding in the presence of heparan sulfate and results in phosphorylation of several tyrosine residues within the cytoplasmic domain of the FGFRs. Phosphorylation of the FGFRs activates the kinase activity and leads to activation of MAPK, PI3 kinase, and Stat1/3 pathways.

Mutations in FGFR genes typically result in gain-of-function mutations, which result in diseases or disorders due to inappropriate activation of the receptors. FGFR mutations have been linked to several developmental disorders, including, e.g., Pfeiffer Syndrome, Jackson-Weiss Syndrome, Crouzon syndrome, Apert Syndrome, Beare-Stevenson Cutis Gyrata Syndrome, Saethre-Chotzen Syndrome, Achondroplasia, Thanatophoric Dysplasia, Hypochondroplasia, Muenke Syndrome, and Severe Achondroplasia with Developmental Delay and Acanthosis Nigricans (SADDAN) dysplasia. FGFRs are also found to be overexpressed in many tumor samples when compared to normal tissues by immunohistochemistry. For example, FGFR overexpression has been identified in primary colorectal cancer, pancreatic cancer, breast cancer, and colon cancer. FGF molecules act as mitogenic, angiogenic, and antiapoptotic factors and are likely involved in carcinogenesis.

The bsBA of the invention can be prepared so that at least one of the two binding molecules of the bsBA specifically binds to an FGFR and prevents or reduces activation of the FGFR, e.g., by blocking ligand binding to the FGFR or by preventing or reducing FGFR dimerization. Such a bsBA can then be used in methods for treating Pfeiffer Syndrome, Jackson-Weiss Syndrome, Crouzon syndrome, Apert Syndrome, Beare-Stevenson Cutis Gyrata Syndrome, Saethre-Chotzen Syndrome, Achondroplasia, Thanatophoric Dysplasia, Hypochondroplasia, Muenke Syndrome, Severe Achondroplasia with Developmental Delay and Acanthosis Nigricans (SADDAN) dysplasia, primary colorectal cancer, pancreatic cancer, breast cancer, and colon cancer by preventing or reducing activation of an FGFR. In a preferred embodiment, the targeting domain of the bsBA is directed to a second receptor that is expressed on the target cell (i.e., a receptor other than the FGFR), which is used to target the bsBA to the target cell.

Platelet-Derived Growth Factor Receptor (PDGFR)

The PDGFR family activates downstream signaling enzymes that stimulate the growth and motility of connective tissue cells, such as vascular smooth muscle cells (VSMCs), oligodendrocytes (cells of the tissue encasing nerve fibers), and chondrocytes (cartilage cells). The PDGF beta receptor is essential for directing the differentiation of VSMCs.

Overexpression of the PDGFR pathway has been linked to a variety of serious diseases, including atherosclerosis and cancer, which are associated with inappropriate or increased activation of the PDGFR. Alternatively, it may be desirable to promote activation of the PDGFR to promote repair of bone, periodontium, ligament, and cartilage.

The bsBA of the invention can be prepared so that at least one of the two binding molecules of the bsBA specifically binds to an PDGFR and prevents or reduces activation of the PDGFR, e.g., by blocking ligand binding to the PDGFR. Such a bsBA can then be used in methods for treating, e.g., atherosclerosis and cancer, by preventing or reducing activation of an PDGFR. In a preferred embodiment, the second binding molecule of the bsBA is directed to a second receptor that is expressed on the target cell (i.e., a receptor other than the PDGFR), which is used to target the bsBA to the target cell. Preferably, the binding molecule of the bsBA that binds the PDGFR has a lower affinity than the affinity that the second binding molecule has for its receptor.

Alternatively, the bsBA of the invention can be prepared so that at least one of the two binding molecules of the bsBA specifically binds to and activates a PDGFR. Such a bsBA can then be used in methods for promoting repair of bone, periodontium, ligament, and cartilage by activating a PDGFR. In a preferred embodiment, the effector domain of the bsBA binds a PDGFR and the targeting domain binds to an antigen or to a second receptor that is known to be expressed on the target cell (e.g., a second, different PDGFR, or a bone-, periodontium-, ligament-, or cartilage-specific receptor).

C-Kit Receptor (Also Known as the Steel Factor Receptor)

The c-Kit proto-oncogene is a transmembrane tyrosine kinase type receptor that is crucial for melanocyte development and proliferation. The proto-oncogene c-Kit encodes a transmembrane tyrosine kinase receptor related to the platelet-derived growth factor PDGF/CSF-1 (c-fms) receptor subfamily. C-Kit has been found to play a pivotal role in the normal growth and differentiation of embryonic melanoblasts. Malignant transformation of melanocytes and progression of human melanoma is associated with the loss of expression of the c-Kit proto-oncogene. The expression of the tyrosine kinase receptor encoded by the c-Kit proto-oncogene gradually declines during the tumor growth and invasion of human melanoma.

The bsBA of the invention can be prepared so that at least one of the two binding molecules of the bsBA specifically binds to and activates the c-Kit receptor. Such a bsBA can then be used in methods for treating, e.g., melanomas. In a preferred embodiment, the targeting domain of the bsBA is directed to an antigen or to a second receptor that is expressed on the target cell (i.e., a receptor other than the c-Kit receptor), which is used to target the bsBA to the target cell.

Fc Receptors (FcR)

Fc receptors are specific cell-surface receptors for antigen-antibody complexes or aggregated immunoglobulins that bind a site in the Fc portion of an immunoglobulin molecule and may exhibit specificity for particular immunoglobulin classes. FcRs are found on B cells, K cells, macrophages, neutrophils, and eosinophils, and, during some developmental stages, on T cells; those on K cells, macrophages, and neutrophils bind to opsonizing antibodies bound to antigens and trigger phagocytosis of the antigen.

Human FcRs are known to be associated with the development or progression of autoimmune diseases (e.g., systemic lupus erythematosus, autoimmune thrombocytopenic purpura, myasthenia gravis, multiple sclerosis, uveitis, and thyroid-associated opthalmopathy) and allergic reaction to allergens. Natural inhibition of FcRs is responsible for maintaining peripheral tolerance, thereby preventing the development of autoimmunity and autoimmune disease. Conversely, deficiency of activation FcRs results in a protective phenotype, uncoupling autoimmunity from autoimmune disease.

The bsBA of the invention can be prepared so that at least one of the two binding molecules of the bsBA specifically binds to an FcR and prevents or reduces activation of the FcR, e.g., by blocking its binding to Ig molecules on immune cells. Such a bsBA can then be used in methods for treating, e.g., autoimmune disease, such as systemic lupus erythematosus, autoimmune thrombocytopenic purpura, myasthenia gravis, multiple sclerosis, uveitis, and thyroid-associated opthalmopathy. Typically, the targeting domain of the bsBA is directed to an antigen or to a second receptor that is expressed on the target cell (i.e., a receptor other than the FcR), which is used to target the bsBA to the target cell.

Use of bsBAs to Bind Cytokine Receptors

In an important group of embodiments, the targeting domain or the effector domain can be used to bind a cytokine receptor on a cell surface. In some embodiments, which are somewhat less preferred, the binding agent can be a natural ligand for the cytokine receptor (for example, IL-13 can be used as a binding agent to bind the IL-13 receptor), or a fragment of such a ligand that retains the ability to bind to the receptor.

Exemplar cytokine receptors (with alternative names shown in parentheses) that can be bound as desired by the targeting domain or the effector domain of the bsBA to effect a useful result in the methods of the invention include:

Cytokine receptor common gamma chain (Gamma-C) (Interleukin-2 receptor gamma chain) (IL-2R gamma chain) (P64) (CD132 antigen);

Interleukin-10 receptor alpha chain (IL-10R-A) (IL-10R1);

Interleukin-10 receptor beta chain (IL-10R-B) (IL-10R2) (Cytokine receptor class-II CRF2-4);

Interleukin-12 receptor beta-1 chain (IL-12R-beta1) (Interleukin-12 receptor beta) (IL-12 receptor beta component) (IL-12RB1);

Interleukin-12 receptor beta-2 chain (IL-12 receptor beta-2) (IL-12R-beta2);

Interleukin-13 receptor alpha-1 chain (IL-13R-alpha-1) (IL-13RA-1) (CD213a1 antigen);

Interleukin-13 receptor alpha-2 chain (Interleukin-13 binding protein);

Interleukin-17 receptor (IL-17 receptor);

Interleukin-17B receptor (IL-17B receptor) (IL-17 receptor homolog 1) (IL-17Rh1) (IL17Rh1) (Cytokine receptor CRL4) (UNQ2501/PRO19612);

Interleukin 21 receptor precursor (IL-21R);

Interleukin-1 receptor, type I (IL-1R-1) (IL-1R-alpha) (P80) (Antigen CD121a);

Interleukin-1 receptor, type II (IL-1R-2) (IL-1R-beta) (Antigen CDw121b);

Interleukin-1 receptor antagonist protein (IL-Ira) (IRAP) (IL1 inhibitor) (IL-1RN) (ICIL-1RA);

Interleukin-2 receptor alpha chain (IL-2 receptor alpha subunit) (P55) (TAC antigen) (CD25 antigen);
Interleukin-2 receptor beta chain (IL-2 receptor) (P70-75) (High affinity IL-2 receptor beta subunit) (CD122 antigen);
Interleukin-3 receptor alpha chain (IL-3R-alpha) (CD123 antigen);
Interleukin-4 receptor alpha chain (IL4R-alpha) (CD124 antigen);
Interleukin-5 receptor alpha chain (IL-5R-alpha) (CD125 antigen)
Interleukin-6 receptor alpha chain (IL-6R-alpha) (IL-6R 1) (CD126 antigen);
Interleukin-6 receptor beta chain (IL-6R-beta) (Interleukin 6 signal transducer) (Membrane glycoprotein 130) (gp130) (Oncostatin M receptor) (CDw130) (CD130 antigen);
Interleukin-7 receptor alpha chain (IL-7R-alpha) (CDw127) (CD127 antigen);
High affinity interleukin-8 receptor A (IL-8R A) (IL-8 receptor type 1) (CXCR-1) (CDw128a);
High affinity interleukin-8 receptor B (IL-8R B) (CXCR-2) (GRO/MGSA receptor) (IL-8 receptor type 2) (CDw128b);
Interleukin-9 receptor (IL-9R);
Interleukin-18 receptor 1 (IL1 receptor-related protein) (IL-1Rrp);
Interleukin-1 receptor-like 1 precursor (ST2 protein);
Interleukin-1 receptor-like 2 (IL-1Rrp2) (Interleukin-1 receptor related protein 2) (IL1R-rp2);
Toll-like receptor 1 (Toll/interleukin-1 receptor-like) (TIL);
Toll-like receptor 2 (Toll/interleukin 1 receptor-like protein 4);
Toll-like receptor 5 (Toll/interleukin-1 receptor-like protein 3);
CX3C chemokine receptor 1 (C-X3-C CKR-1) (CX3CR1) (Fractalkine receptor) (GPR13) (V28) (Beta chemokine receptor-like 1) (CMK-BRL-1) (CMKBLR1);
C-X-C chemokine receptor type 3 (CXC-R3) (CXCR-3) (CKR-L2) (CD183 antigen);
C-X-C chemokine receptor type 4 (CXC-R4) (CXCR-4) (Stromal cell-derived factor 1 receptor) (SDF-1 receptor) (Fusin) (Leukocyte-derived seven transmembrane domain receptor) (LESTR) (LCR1) (FB22) (NPYRL) (HM89) (CD184 antigen);
C-X-C chemokine receptor type 5 (CXC-R5) (CXCR-5) (Burkitt'S lymphoma receptor 1) (Monocyte-derived receptor 15) (MDR15);
C-X-C chemokine receptor type 6 (CXC-R6) (CXCR-6) (G protein-coupled receptor bonzo) (G protein-coupled receptor STRL33);
Chemokine binding protein 2 (Chemokine-binding protein D6) (C-C chemokine receptor D6) (Chemokine receptor CCR-9) (CC-Chemokine receptor CCR10);
C-C chemokine receptor type 1 (C-C CKR-1) (CC-CKR-1) (CCR-1) (CCR1) (Macrophage inflammatory protein-1 alpha receptor) (MIP-1alpha-R) (RANTES-R) (HM145) (LD78 receptor);
C-C chemokine receptor type 2 (C-C CKR-2) (CC-CKR-2) (CCR-2) (CCR2) (Monocyte chemoattractant protein 1 receptor) (MCP-1-R);
C-C chemokine receptor type 3 (C-C CKR-3) (CC-CKR-3) (CCR-3) (CCR3) (CKR3) (Eosinophil eotaxin receptor);
C-C chemokine receptor type 4 (C-C CKR-4) (CC-CKR4) (CCR4) (CCR4) (K5-5);
C-C chemokine receptor type 5 (C-C CKR-5) (CC-CKR-5) (CCR-5) (CCR5) (HIV-1 fusion coreceptor) (CHEMR13) (CD195 antigen);
C-C chemokine receptor type 6 (C-C CKR-6) (CC-CKR-6) (CCR-6) (LARC receptor) (GPR-CY4) (GPRCY4) (Chemokine receptor-like 3) (CKR-L3) (DRY6);
C-C chemokine receptor type 7 precursor (C-C CKR-7) (CC-CKR-7) (CCR-7) (MIP-3 beta receptor) (EBV-induced G protein-coupled receptor 1) (EBI1) (BLR2);
C-C chemokine receptor type 8 (C-C CKR-8) (CC-CKR-8) (CCR-8) (GPR-CY6) (GPRCY6) (Chemokine receptor-like 1) (CKR-L1) (TER1) (CMKBRL2) (CC-chemokine receptor CHEMR1);
C-C chemokine receptor type 9 (C-C CKR-9) (CC-CKR-9) (CCR-9) (GPR-9-6);
C-C chemokine receptor type 10 (C-C CKR-10) (CC-CKR-10) (CCR-10) (G-protein coupled receptor 2);
C-C chemokine receptor type 11 (C-C CKR-11) (CC-CKR-11) (CCR-11) (Chemokine receptor-like 1) (CCRL1) (CCX CKR);
Chemokine receptor-like 1 (G-protein coupled receptor DEZ) (G protein-coupled receptor ChemR23),
Chemokine receptor-like 2 (IL8-related receptor DRY12) (Flow-induced endothelial G protein-coupled receptor) (FEG-1) (G protein-coupled receptor GPR30) (GPCR-BR);
Chemokine XC receptor 1 (XC chemokine receptor 1) (Lymphotactin receptor) (G protein-coupled receptor 5).

Use of bsBAs to Bind Tumor-Associated Antigens

In a particularly important group of embodiments, the targeting domain of the bsBAs bind to a tumor-associated antigen. As the name implies, tumor-associated antigens (TAA) are typically antigens that are expressed on cells of particular tumors, but that are typically not expressed in normal cells. Often, TAA are antigens that are normally expressed in cells only at particular points in an organism's development (such as during fetal development) and that are being inappropriately expressed in the organism at the present point of development, or are antigens not expressed in normal tissues or cells of an organ now expressing the antigen. A number of TAA are known in the art, including MART-1, carcinoembryonic antigen ("CEA"), gp100, MAGE-1, HER-2, and Lewis$^Y$ antigens, and antigens identified in, e.g., U.S. Pat. Nos. 5,922, 566 and 6,020,478 and WO 2004/016643 A2.

Other tumor-associated antigens suitable for targeting with the bsBA of the invention include:

hematopoietic differentiation antigens—glycoproteins usually associated with cluster differentiation (CD) groupings, such as CD5, CD19, CD20, CD22, CD33, CD45, CD52, and CD147;

cell surface differentiation antigens, including glycoproteins, such as carcinoembryonic antigen (CEA, Swiss-Prot ID No. P06731), tumor associated glycoprotein (TAG-72, also identified as CA72-4, see, e.g., Hombach et al., Gastroenterology. 113 (4):1163-70 (1997)), polymorphic epithelial mucin (PEM), epithelial cell adhesion molecule (Ep-CAM, MUC-1, A33, G250, E-cadherin, prostate-specific membrane antigen (PSMA, Swiss-Prot ID No. Q04609) and prostate-specific antigen (PSA), glycolipids, such as gangliosides, e.g., GD2, GD3, GM2) and carbohydrates, such as blood group-related antigens, including LE$^Y$ and LE$^b$ (LE$^Y$ is "LewisY", also known as "CD174"; it is a difucosylated tetrasaccharide found on the type 2 blood group oligosaccharides of glycolipids and glycoproteins);

growth factor receptors, including epidermal growth factor receptor (EGFR, ErbB1, Swiss-Prot ID P00533) and its mutant form EGFRvIII, ErbB2 (HER-2/neu, Swiss-Prot ID No. P04626), ErbB3 (HER-3, Swiss-Prot ID No. P21860) and IL-2 receptor.

angiogenesis and stromal antigens, including fibroblast activation protein (FAP), vascular endothelial growth factor receptor (VEGFR), tenascin and integrin; and, the Frizzled receptor family (e.g. Fz-2)

In some embodiments, the targeting domain of the bsBA is targeted to bind the TAA, while the effector domain binds to a growth factor receptor.

In some preferred embodiments, the targeting domain is targeted to a molecule selected from CEA (Swiss-Prot ID No. P06731), ErbB2 (Swiss-Prot ID No. P04626), EGFR (Swiss-Prot ID No. P00533), LewisY, MUC-1 (Swiss-Prot ID No. P15941), EpCAM (the target of mAb 17-1A (edrecolomab, Panorex®, Glaxo Wellcome GmbH)), CA125 (Swiss-Prot ID No. Q96RK2), PSMA (Swiss-Prot ID No. Q04609), TAG72, CD20 (Swiss-Prot ID No. P11836), CD19 (Swiss-Prot ID No. P15391), CD22 (Swiss-Prot ID No. P20273), and CD36 (Swiss-Prot ID No. P16671). It should be noted that the CD antigens in particular are frequently expressed on normal cells but are overexpressed on or a marker for certain cancers.

In some preferred embodiments, the effector domain binds to a molecule selected from ErbB3 (Swiss-Prot ID No. P21860), ErbB4 (Swiss-Prot ID No. Q15303), FGF receptors 1-4 (Swiss-Prot ID Nos. P22455, P11362, P21802, P22607), HGF receptor (Swiss-Prot ID No. P08581), IGF1-R (Swiss-Prot ID No. P08069). Insulin receptor (Swiss-Prot ID No. P06213), PDGF receptors alpha and beta (Swiss-Prot ID Nos. P16234, P09619, respectively) and C-KIT (Swiss-Prot ID No. P10721). In some particularly preferred embodiments, the targeting domain binds to a molecule as described in the preceding paragraph and the effector domain binds to a molecule described in this paragraph.

Aptamers

BsBAs in which one or both of the binding molecules are aptamers can be prepared as described in U.S. Pat. No. 5,756,291, incorporated herein by reference. Aptamers are usually prepared by the "SELEX" (short for "systematic evolution of ligands by exponential enrichment") method. This is an iterative process used to identify an aptamer to a chosen molecular target. To begin, a large "library" of nucleic acid molecules is generated. In a selection step the molecules with the greatest affinity for the target of interest are isolated. The library of nucleotide sequences is exposed to the cell surface protein and allowed to incubate for a period of time. The molecules in the library with weak or no affinity for the target are washed away and the target-bound molecules, among which are the highest affinity aptamers, are purified away from the target and used for the subsequent steps in the SELEX process.

The captured, purified sequences are copied enzymatically, or "amplified", to generate a new library of molecules that is substantially enriched for those that can bind to the target. The enriched library is used to initiate a new cycle of selection, partitioning and amplification. After 5-15 cycles of the complete process, the library of molecules is reduced from $10^{15}$ of unique sequences to a small number that bind tightly to the cell surface protein of interest. Individual molecules in the mixture are then isolated, their nucleotide sequences are determined, and their properties with respect to binding affinity is measured essentially as for antibodies. Often the aptamers are further refined to eliminate any nucleotides that do not contribute to target binding or aptamer structure. Aptamers truncated to their core binding domain typically range in length from 15 to 60 nucleotides. Two aptamers may be linked by a nucleotide linker or chemically cross linked to form bi-specific aptamers or a single aptamer may be similarly linked to an antibody or antibody fragment to form a chimeric antibody-DNA molecule.

Creating Bi-Specific BAs by Chemical Cross Linking

The two binding molecules of bispecific blocking agents, such as bispecific antibodies, can be joined using conventional conjugation methods known to the skilled artisan, such as those described in Hermanson, supra. In some embodiments, the two binding molecules of the bsBA are joined using chemical linkages. One example of a prior bispecific antibody prepared using a chemical linkage is described by Brennan et al., (Science, 229: 81 (1985)), and can also be used to prepare bsBAs of the present invention. Intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Another preferred chemical linkage employs bis-maleimidohexane or bi-maleimidoethane for cross-linking. Antibody fragments containing —SH groups for cross-linking can also be prepared recombinantly (e.g. Shalaby et al., J. Exp. Med., 175: 217-225 (1992)) to avoid proteolytic cleavage of full length antibodies.

Creating bsBAs by Recombinant or Synthetic Techniques

BsBAs can also be prepared by recombinant techniques. Nucleic acid sequences encoding the bsBAs can be prepared by any suitable method including, for example, cloning of appropriate sequences or by direct chemical synthesis by methods such as the phosphotriester method of Narang, et al., Meth. Enzymol. 68:90-99 (1979); the phosphodiester method of Brown, et al., Meth. Enzymol. 68:109-151 (1979); the diethylphosphoramidite method of Beaucage, et al., Tetra. Lett. 22:1859-1862 (1981); the solid phase phosphoramidite triester method described by Beaucage & Caruthers, Tetra. Letts. 22 (20):1859-1862 (1981), e.g., using an automated synthesizer as described in, for example, Needham-VanDevanter, et al. Nucl. Acids Res. 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, nucleic acid sequences encoding bsBAs are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and John Wiley & Sons, Inc., (1987, 1995 Supplement) (Ausubel)). Product information from manufacturers of biological reagents and experimental equipment also provide useful information. Such manufacturers include the SIGMA chemical company (Saint Louis, Mo.), R&D systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Once nucleic acids encoding a bsBA are cloned, one may express the desired protein in a recombinantly engineered cell such as bacteria, plant, yeast, insect and mammalian cells. It is expected that those of skill in the art are knowledgeable in the numerous expression systems available for expression of proteins including E. coli, other bacterial hosts, yeast, and various higher eukaryotic cells such as the COS, CHO, HeLa and myeloma cell lines. No attempt to describe in detail the various methods known for the expression of proteins in prokaryotes or eukaryotes will be made.

One of skill would recognize that modifications can be made to a nucleic acid encoding a bsBA without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation site, and additional amino acids placed on either terminus to create conveniently located restriction sites.

In addition to recombinant methods, the bsBAs can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield, et al. J. Am. Chem. Soc. 85:2149-2156 (1963), and Stewart, et al., Solid Phase Peptide Synthesis, 2nd ed., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicyclohexylcarbodiimide) are known to those of skill.

Once expressed, the recombinant bsBAs can be purified according to standard procedures of the art, including ammonium sulfate precipitation, affinity columns, column chromatography, and the like (see, generally, R. Scopes, Protein Purification, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as E. coli have been described and are well-known and are applicable to the bsBAs of this invention, particularly those which employ antibodies. See, Buchner, et al., Anal. Biochem. 205:263-270 (1992); Pluckthun, Biotechnology 9:545 (1991); Huse, et al., Science 246:1275 (1989) and Ward, et al., Nature 341:544 (1989), all incorporated by reference herein.

Often, functional heterologous proteins from E. coli or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., Biochemistry 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M 1-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

BsBA-Based Therapeutic Uses

The present invention is further directed to bsBA-based therapies which involve administering bsBAs of the invention to an animal, preferably a mammal, and most preferably a human patient, for treating one or more of the described diseases or disorders. Therapeutic compounds of the invention include, but are not limited to, bsBAs of the invention. The bsBAs of the invention can be used to treat, inhibit, or prevent the diseases and disorders disclosed herein that are associated with aberrant expression and/or activity of a cell surface receptor. The treatment and/or prevention of diseases and disorders associated with aberrant expression and/or activity of a cell surface receptor includes, but is not limited to, alleviating symptoms associated with those diseases and disorders. BsBAs of the invention may be provided in pharmaceutically acceptable compositions as known in the art or as described herein. Armed with the teachings provided herein, one of ordinary skill in the art will know how to use the bsBAs of the present invention for diagnostic, monitoring, or therapeutic purposes without undue experimentation.

The bsBAs of the invention may be administered alone or in combination with other types of treatments (e.g., radiation therapy, chemotherapy, hormonal therapy, immunotherapy and anti-tumor agents).

BsBA-Based Therapeutic/Prophylactic Composition and Administration Thereof

The invention provides methods of treatment, inhibition, and prophylaxis by administration to a subject of an effective amount of a bsBA of the invention, preferably a bispecific antibody of the invention. In a preferred aspect, the bsBA is substantially purified (e.g., substantially free from substances that limit its effect or produce undesired side effects). The subject is preferably an animal, including but not limited to animals such as cows, pigs, horses, chickens, cats, and dogs, and is preferably a mammal, and most preferably a human.

Various delivery systems are known and can be used to administer a bsBA of the invention, e.g., encapsulation in liposomes, microparticles, microcapsules, recombinant cells capable of expressing the bsBA, receptor-mediated endocytosis (see, e.g., Wu and Wu, J. Biol. Chem. 262:4429-4432, 1987), construction of a nucleic acid as part of a retroviral or other vector, etc. Methods of introduction include but are not limited to intradermal, intramuscular, intraperitoneal, intravenous, subcutaneous, intranasal, epidural, and oral routes.

The bsBAs may be administered by any convenient route, for example by infusion or bolus injection, by absorption through epithelial or mucocutaneous linings (e.g., oral mucosa, rectal and intestinal mucosa, etc.), and may be administered together with other biologically active agents. Administration can be systemic or local. In addition, it may be desirable to introduce the bsBA of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the bsBAs of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a bsBA of the invention, e.g., an antibody, care must be taken to use materials to which the bsBA does not absorb.

In another embodiment, the bsBA can be delivered in a vesicle, in particular a liposome (see Langer, Science 249: 1527-1533, 1990; and Treat et al., in Liposomes in the Therapy of Infectious Disease and Cancer, Lopez-Berestein and Fidler (eds.), Liss, New York, pp. 353-365, 1989).

In yet another embodiment, the bsBA can be delivered in a controlled release system. In one embodiment, a pump may be used (see Langer, supra; Sefton, CRC Crit. Ref. Biomed. Eng. 14:201, 1987; Buchwald et al., Surgery 88:507, 1980; Saudek et al., N. Engl. J. Med. 321:574, 1989). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, e.g., an affected organ of the body, such as the brain, lungs, kidney, liver, ovary, testes, colon, pancreas, breast, and skin, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249: 1527-1533).

The present invention also provides bsBAs provided in a pharmaceutical composition. Such compositions comprise a therapeutically effective amount of a bsBA and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington: The Science and Practice of Pharmacy," A. R. Gennaro, ed. Lippincott Williams & Wilkins, Philadelphia, Pa. (20th Ed., 2003). Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The bsBAs, when formulated in pharmaceutical compositions, can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, or procaine.

The amount of the bsBA of the invention that will be effective in the treatment, inhibition and prevention of a disease or disorder associated with aberrant expression and/or activity of a cell surface receptor can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For bsBAs, the dosage administered to a patient is typically 0.1 mg/kg to 100 mg/kg of the patient's body weight. Preferably, the dosage administered to a patient is between 0.1 mg/kg and 20 mg/kg of the patients body weight, more preferably 1 mg/kg to 10 mg/kg of the patient's body weight. Generally, human antibodies have a longer half-life within the human body than antibodies from other species due to the immune response to the foreign polypeptides. Thus, bsBAs derived from human antibodies can be administered in smaller dosages and with less frequent administration. Further, the dosage and frequency of administration of bsBAs of the invention may be reduced by enhancing uptake and tissue penetration of the antibodies by modifications such as, for example, lipidation.

Kits

The present invention further encompasses kits for use in detecting cells expressing or overexpressing target molecules in vivo, or in biological samples. In some preferred embodiments, the kits contain bsBAs targeted by bispecific scFv antibodies. Depending on use, the antibodies can be functionalized with linkers or chelators, or both, for coupling to an effector (e.g. a radioactive moiety, a liposome, a cytotoxin, another antibody, etc.) as described herein. The kits optionally further comprise buffers and compositions to be used for detection of the bsBAs.

The kits can also include instructional materials teaching the use of the antibodies for detecting, e.g. cancer cells, and/or teaching the combination of the antibodies with functionalizing reagents or teaching the use of functionalized antibodies for imaging and/or therapeutic applications. In certain embodiments, the bsBA is provided functionalized with a linker and/or a chelator (in one container) along with one or more effectors, e.g. cytotoxins, radioactive labels (in a second container) such that the two components can be separately administered (e.g. in pre-targeting approaches) or such that the two components can be administered shortly before use.

Certain instructional materials will provide recommended dosage regimen, counter indications, and the like. While the instructional materials typically comprise written or printed materials, any medium capable of storing such instructions and communicating them to an end user is contemplated by this invention. Such media include, but are not limited to electronic storage media (e.g., magnetic discs, tapes, cartridges, chips), optical media (e.g., CD ROM), and the like, or internet locations that provide the instructions. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

Example 1

Diabodies and (scFv)$_2$

The production of diabodies is disclosed, for example, in EP 404,097; WO 93/11161; and Hollinger et al. (Proc. Natl. Acad. Sci. USA, 90:6444-6448 (1993)). Diabodies are constructed from antibody fragments, usually from two scFvs, by using a linker that is too short to allow pairing between the two domains on the same chain; the domains are forced to pair with the complementary domains of another chain and create two antigen-binding sites. Alternatively, two scFv's may be linked by a genetically encoded linker that covalently links the two molecules thereby forming a (scFv)$_2$ that is a bivalent antibody.

Example 2

Different types of "dimerization domains" may be used to heterodimerize two antibody fragments. For instance, by genetically fusing a bispecific/divalent diabody to, via the hinge region, the N-terminus of the CH(3) domain of an IgG (Lu et al. J Immunol Methods. 279 (1-2):219-32 (2003)), creating a construct termed a "di-diabody". The result is a tetravalent diabody dimer resulting from dimerization between the hinge region and the CH(3) domains.

The natural CH1 domain of an antibody may also be used to heterodimerize two antibody fragments by genetically fusing a single-chain Fv (scFv) to the C-terminus of either the light chain or the heavy chain of a Fab fragment of different antigen-binding specificity (Lu et al. Immunol Methods. 267 (2):213-26 (2002)). The natural dimerization mechanism between IgG heavy and light chains may also be used. Two single-chain Fv (scFv) of different specificity can be fused to the constant domain of human kappa chain (C(L)) and the first constant domain of human heavy chain (C(H1)), to form two polypeptides, (scFv)(1)-C(L) and (scFv)(2)-C(H1)-C(H2)-C(H3), respectively. Co-expression of the two polypeptides in mammalian cells results in the formation of a covalently linked IgG-like hetero-tetramer, Bs(scFv)(4)-IgG, with dual specificity (Zuo et al. Protein Eng. 13 (5):361-7 (2000), Lu et al. J. Biol Chem. 23; 279 (4):2856-65 (2004)).

Heterodimer formation of two antibody fragments may also be forced through non-covalent interaction in a dimerization domain, e.g. with heterodimer-forming leucine zippers Fos and Jun that can mediate the formation of bispecific F(ab')$_2$ when they are fused separately to two different Fab' fragments (Tso et al J. Hematother. 4 (5):389-94 (1995)).

Example 3

Determining Suitable Target and Effector Markers

Suitable target markers may be determined in a number of ways such as by mRNA profiling of target and non-target tissue to identify target molecules that are over-expressed in target tissue, or by proteomic methods such as 2D electrophoresis of target and non-target cells for comparison of protein expression levels and subsequent identification by mass spectroscopy. For example, mRNA profiling typically employs Affymetrix microarrays and is performed as described in Cao et al (BMC Genomics. 27; 5 (1):26 (2004)) by comparing cRNA prepared from target and non-target tissue (e.g. tumor and adjacent normal tissue).

In proteomic methods, target and non-target cells are typically lysed or homogenized and then subjected to electrophoresis in two dimensions. The proteins are then fixed in the gel and stained for visualization. Image analysis of the gels from the target and non-target cells can reveal proteins spots than are differentially expressed. These spots can then be identified by excision of the protein spot, in-gel trypsin digestion, and analysis by mass spectrophotometer. The process is described in, for example, Van Greevenbroek et al. 45, 1148-1154 (2004).

Suitable effector markers can be identified in a number of ways, such as by identifying receptors with putative phosphorylation sites. Protein or DNA sequences can be obtained from GenBank or other public databases and potential phosphorylation sites can be predicted by publicly available search engines, such as ScanSite (found on-line by entering "http://", followed by "scansite.mit.edu/") or NetPhos (found on the web by entering "www." followed by "cbs.dtu.dk/services/NetPhos/"). Receptors with phosphorylation sites are more likely to be good effector markers since these are often involved in signaling. Alternatively, suitable effector markers may be identified by contacting target cells with antibodies to markers on the cell and then assaying for the desired biological activity as described above.

Example 4

Testing Univalent and Bivalent Binding Domains

To test the univalent affinity of the binding domains or of the bispecific binding molecule, bsBAs are produced as described above. To measure the binding kinetics by surface plasmon resonance, a biosensor chip can activated for covalent coupling of the receptor using N-ethyl-N'-(3-dimethylaminopropyl)-carbodiimide hydrochloride (EDC) and N-hydroxysuccinimide (NHS) according to the manufacturer's (BIAcore) instructions. The marker is then coupled e.g. by injection in 10 mM sodium acetate buffer (pH 4.5) to obtain a signal of ideally less than 400 response units (RU) of immobilized material. For kinetics measurements, two-fold serial dilutions of the univalent or bispecific binding domain is injected over the antigen chip in PBS/Tween buffer (0.05% Tween-20 in phosphate buffered saline) at 25° C. using a flow rate of 20 μl/min. Dissociation data is then fit to a one-site model to obtain $k_{off}$ and the pseudo-first order rate constant (ks) can be calculated for each association curve, and plotted as a function of protein concentration to obtain $k_{on}$+/−s.e. Equilibrium dissociation constant, $K_d$ can then be calculated from SPR measurements as $k_{off}/k_{on}$. The absence of experimental artifacts, such as rebinding of dissociated bsBA, must be determined by performing above measurements on several surfaces of different densities, e.g., 100, 200, and 400 RU.

Alternatively, their affinities may also be determined by flow cytometry as described in, for example, Nielsen et al. (Cancer Res. 60 (22):6434-40 (2000)).

Example 5

Measuring Effector Function in Cells

Effector function of a binding domain can be determined by contacting target cells grown in culture with the effector binding domain at different concentrations for e.g. 30 minutes. At this point the cells are in some cases stimulated with exogenous growth factor to promote the biological effect that the molecule seeks to alter. Extracts of the treated cells, grown in 6- or 12-well tissue culture plates, are prepared by passing cells 5 times through a 27 G needle in lysis buffer (20 mM Tris (pH 7.5), 150 mM NaCl, 1 mM EDTA, 1 mM EGTA, 1% Triton X-100, 0.5% NP40, 10 mM β-glycerolphosphate, 10 mM NaF, 1 mM $Na_3VO_4$ containing protease inhibitors (1 mM PMSF, 1 μg/mL Leupeptin, 1 μg/mL Pepstatin) on ice. Before lysis, cells are washed twice in cold PBS. The lysates are then analyzed e.g. by immunoblotting with phospho-specific antibodies: Total cell protein extracts (50 μg of total proteins/lane) is resolved by electrophoresis using 7.5% SDS-PAGE precast gels (Invitrogen, Carlsbad, Calif.), transferred to nitrocellulose filters, and incubated with antibodies that detect activation of the marker or downstream associated proteins. Alternatively, the lysates may be analyzed by antibody microarrays as described in Nielsen et al. (Proc Natl Acad Sci USA. 100 (16):9330-5 (2003)).

Effector function of a binding domain may also be determined by other readouts of the desired biological function e.g. cell proliferation assays. Target cells can be seeded at $5 \times 10^3$ per well in a 96-well dish containing DMEM and 5% FCS and varying concentrations of binding domain. After 72 h, the cells are lysed and the amount of ATP can be determined by CellTiter-Glo Luminescent Cell Viability Assay (Promega, Madison, Wis.) according to the manufacturer's protocol.

The results of the phosphorylation and proliferation assays can be plotted with degree of inhibition as a function of the log of the concentration and the $IC_{50}$ determined for the effector and targeting domains by fitting to the equation:

$$Y = \text{Bottom} + \frac{(\text{Top} - \text{Bottom})}{1 + 10^{LogEC50-X}}$$

Example 6

Testing of BsBAs

To test the effect of a bsBA for its ability to prevent, reduce, or inhibit cell signaling mediated by ErbB receptors, cancer cells such as A431 (an estrogen dependent breast cancer cell line, National Center for Biotechnology Information Accession GDS121) are incubated with bsBAs at various concentrations for 30 minutes before challenging the cells with growth factors (e.g., heregulin or EGF) for up to two hours. Cells are then lysed in Triton buffer followed by sonication. The lysates are then analyzed for changes in phosphorylation either by immunoblotting or using antibody microarrays that are sensitive to phosphorylation of proteins (see, e.g., Nielsen et al., 2003, PNAS 100:9330).

For instance, our computational modeling predicts that a bsBA with a targeting domain that binds to a cell surface antigen expressed at 1 million copies per cell with an affinity of 1 nM and an effector domain that binds to ErbB3 (and therefore competes for heregulin binding) with 1 μM affinity, will be as effective (as measured by $IC_{50}$) as a bsBA with a targeting domain and an effector domain that both bind with 1 nM affinity.

BsBAs can be used for inhibition of the growth of cancers that express appropriate antigens. The effect of the bsBAs can be augmented by conjugating small molecule drugs to the bsBA. The drugs can be, for example, standard cytotoxic agents, such as a chemotherapeutic, or tyrosine kinase inhibitors, such as Gleevec® (imatinib mesylate).

Example 7

ErbB BsBAs

Computer simulation of the heregulin (HRG)-induced ERK and AKT activation in A431 cells showed that ErbB bsBAs are most efficient if one of the ErbB receptor binding molecules of the bsBA has a lower affinity for its receptor than the other ErbB binding molecule has for its receptor.

If the low affinity binding molecule of the bsBA of the invention is directed to either ErbB3 or ErbB4 and the high affinity binding molecule of the bsBA is directed to another ErbB receptor (e.g., ErbB1 or ErbB2), the bsBA reduces, prevents, or inhibits cell signaling mediated by the ErbB receptors by, it is believed, sequestering ErbB3 or ErbB4 into a trimeric complex consisting of the ErbB3 or ErbB4 receptor, the bsBA, and an ErbB1 or ErbB2 receptor (i.e., ErbB3/4:bsBA:ErbB1/2).

The binding molecules of the bsBA can also be directed to ErbB3 and ErbB4. Such a bsBA is believed to inhibit the dimerization of these ErbB receptors with ErbB1 or ErbB2. Because the dimerization of ErbB3 or ErbB4 with ErbB1 or ErbB2 is necessary for signal transduction, the bsBA effectively prevents; reduces, or inhibits cell signaling by blocking formation of the dimer. Preferably, the low affinity binding molecule of this bsBA binds to ErbB3.

The binding molecules of the bsBA can be prepared so that they bind to ErbB1 and ErbB2, thereby crosslinking these two receptors. This bsBA functions by reducing, preventing, or inhibiting dimerization of ErbB1 and ErbB2 with ErbB3 or ErbB4, which, as is discussed above, is necessary for signal transduction. Preferably, the low affinity binding molecule of this bsBA binds to ErbB1.

Exemplar bsBAs include a low affinity binding molecule that binds to ErbB3 with a high binding molecule for EGFR or ErbB4. BsBAs can also be used to localize cytotoxic or chemotherapeutic agents to cells which express an ErbB receptor. These agents possess two binding molecules, each of which is specific for a different ErbB receptor, and a cytotoxic or chemotherapeutic agent (e.g. saporin, anti-interferon-α, vinca alkaloid, ricin A chain, methotrexate or radioactive isotope hapten) conjugated to the bsBA. BsBAs can be prepared as full length antibodies or antibody fragments (e.g. $F(ab')_2$ or $(Fv)_2$ bispecific antibodies), diabodies, or as an aptamer with two different binding molecules.

The model has been tested using the ErbB family of receptors. Stimulation of the ErbB receptors with EGF or HRG leads to the simultaneous activation of the pathways leading to phosphorylation of ERK and AKT, which crosstalk on various levels within the signal cascade. The sensitivity of analysis enables us to apportion the uncertainty of the model output to different sources of uncertainty in the model input. As tumor cells are characterized by distinct receptor expression levels, we identified ErbB3 and ErbB4 as very sensitive targets when HRG was the ligand.

In general, when the binding molecules of the bsBA are antibodies, or fragments thereof, these binding molecules can be well characterized biochemically because their dissociation constants or even the association and dissociation rates can be easily determined. Likewise, the mechanism of action of antibodies can be easily described using a mathematical model and the effect of using a known antibody as an inhibitor can be tested in silico. Using our computational model, we tested the idea of using bispecific antibodies (i.e., an antibody that has two distinct binding molecules, in which each binding region binds a different ErbB receptor) to block the ErbB cell signaling pathway. The in silico results confirm that an antibody having binding specificity for two different ErbB receptors, in which the binding affinity for one ErbB receptor is greater than the binding affinity for the other ErbB receptor, is ideal for blocking or preventing cell signaling through the ErbB pathway.

Using an in silico approach, we compared the ability of bispecific antibodies that target two different ErbB receptors to block or prevent activation of the ErbB signaling pathway in three different cell lines that exhibit differential expression of ErbB receptors (Table 1) versus the ability of conventional inhibitors that target only one ErbB receptor. Signal inhibition in each cell line was modeled in silico for bispecific antibodies, as well as for current therapeutic monospecific antibodies. Our model predicted that inhibition of cellular signaling by bispecific antibodies that have a differential affinity for two different ErbB receptor would be much higher than the inhibition of cellular signaling mediated by traditional single receptor inhibitors. The data generated by our computer modeling is shown in Table 2. Depending on the receptor ratios present in tumors, distinct bsAbs, having a high affinity binding molecule and a low affinity binding molecule, are predicted to be substantially more potent inhibitors than monospecific antibodies or bispecific antibodies in which both binding molecules bind to their respective antigens with the same binding affinity.

TABLE 1

Receptor expression profiles of ErbB receptors on different cell lines

|  | Cell Type A | Cell Type B | Cell Type C |
|---|---|---|---|
| ErbB1 | xxx | xx | x |
| ErbB2 | xx | xxx | xx |
| ErbB3 | x | xx | x |
| ErbB4 | — | xx | x |

TABLE 2

Inhibition by BsBA compared to traditional monospecific receptor inhibitors

|  |  | BsAb(1-2) ERK\|AKT | BsAb(1-3/4) ERK\|AKT | BsAb(2-3/4) ERK\|AKT | BsAb(3-4) ERK\|AKT | ErbB1-Inh ERK\|AKT | ErbB2-Inh ERK\|AKT | ErbB3/4-Inh ERK\|AKT |
|---|---|---|---|---|---|---|---|---|
| Cell Type A | EGF | +\|+ | ++\|++ | −−\|+ | −−\|+ | +\|+ | −−\|−− | −−\|+ |
|  | HRG | +\|+ | ++\|++ | ++\|++ | −−\|−− | −−\|−− | +\|+ | +\|+ |
| Cell Type B | EGF | +\|+ | ++\|++ | −−\|+ | −−\|+ | +\|+ | −−\|−− | −−\|+ |
|  | HRG | +\|+ | +\|+ | ++\|++ | +\|+ | −−\|−− | +\|+ | +\|+ |
| Cell Type C | EGF | +\|+ | ++\|++ | −−\|++ | −−\|+ | +\|+ | +\|+ | −−\|+ |
|  | HRG | +\|+ | ++\|++ | ++\|++ | +\|+ | −−\|−− | +\|+ | +\|+ |

We identified a bispecific antibody against ErbB1 (high affinity) and ErbB3 or ErbB4 (low affinity) as the most effective blocking agent for preventing cell signaling due to activation of the ErbB pathway under all stimulation conditions. An ErbB1-ErbB2 bsAb was also quite effective as a ErbB cell signaling blocking agent under all stimulation conditions. When HRG was used as the activating agent, an ErbB3-ErbB4 bsAb is a very effective blocking agent of the ErbB pathway. Therefore, a preferred bsBA is one in which at least one feature of the blocking agent is the ability to target an ErbB3 or ErbB4 receptor (using a low affinity binding molecule). In fact, with the help of the computational model, we have identified the strong signaling properties of ErbB3/4. Cross-linking ErbB3/4 to themselves, or to a more typical cancer antigen such as ErbB1 or ErbB2, serves as mechanism to inhibit ErbB3/4 signaling by either the simultaneous inhibition of two receptors or the sequestration of the receptors.

One of the benefits associated with using a bsBA, rather than a traditional monospecific blocking agent, such as an monospecific antibody, is that the bispecific blocking agent forms stable trimers (i.e., ErbB receptor-bispecific blocking agent-ErbB receptor). Therefore, the efficiency of the bsBA is much higher than that of a traditional single receptor inhibitor, as shown in Table 2.

By binding to two different ErbB receptors, the bsBA of the invention sequesters the ErbB receptor from interacting with the same or a different ErbB receptor. The bsBAs form a very stable (irreversible) trimer complex that prevents, reduces, or inhibits the cell signaling activities of the bound ErbB receptors. The initial binding step of the bsBA to either ErbB1, ErbB2, ErbB3, or ErbB4 can be a reversible step and the second binding step to the remaining ErbB receptor leads to the formation of a very stable trimer. Alternatively, the first binding step of the bsBA to either ErbB1, ErbB2, ErbB3, or ErbB4 may be irreversible and the second binding step is reversible, thereby allowing the bsBA to form multiple different trimer complexes. The formation of an ErbB receptor: bsBA:ErbB receptor trimer results in a complex that cannot induce cell signaling. Furthermore, by sequestering ErbB1, ErbB2, ErbB3, and ErbB4, the bsBA prevents, reduces, or inhibits dimerization of these ErbB receptors with the same or a different ErbB receptor. Preferably, the bsBA has a higher affinity for ErbB1 or ErbB2 and a lower affinity for ErbB3 or ErbB4, provided that when one binding domain of the bsBA has a high affinity for ErbB2, the second binding domain does not bind to ErbB3.

The formation of an incomplete bsBA-ErbB receptor dimer, in which only one of the two binding molecules of the bsBA is engaged, does not result in a complex that impairs cell signaling; only the formation of the trimeric complex (i.e., ErbB receptor:bsBA:ErbB receptor) prevents cell signaling. Furthermore, trimer formation is not possible between two ErbB receptors that are bound by a bsBA.

Other characteristics of a bsBA include the ability of one binding domain to reduce, prevent, or inhibit cell signaling by competing with the natural ligand for the ErbB receptor, such as HRG.

Our in silico data demonstrate that an ErbB3-ErbB4 bsBA is more efficient at blocking cell signaling than a monospecific ErbB3 or ErbB4 inhibitor. A monospecific inhibitor directed solely to ErbB3 or ErbB4 does not inhibit AKT phosphorylation as effectively as the ErbB3-ErbB4 bsBA, primarily due to the high cell surface expression level of ErbB3 and ErbB4. AKT phosphorylation is only prevented when both an ErbB3 and an ErbB4 monospecific inhibitor are used.

Because the bsBA does not have any inhibitory effect in an unbound state or as dimeric complex with only one ErbB receptor, an increase in the inhibitor concentration, such that the ErbB receptors become saturated with bsBA, results in a decrease in the inhibitory effect of the bsBA. This effect can be reversed by providing a bsBA that has an increased affinity of for ErbB2, such that the binding affinity of the bsBA is greater for ErbB3 than for ErbB4 (i.e., KdErbB3>ErbB4).

The bsBAs discussed above are particularly efficient in a HRG dominated regime. In general the bsBAs are efficient at much lower doses compared to ErbB receptor inhibitors that target only one receptor.

Another preferred embodiment of the present invention is a bsBA in which one binding molecule of the bsBA has binding specificity for ErbB1 (high affinity binding) and the other binding molecule has binding specificity for ErbB3 or ErbB4 (low affinity binding). In general, tumor cells express high amounts of ErbB1 (i.e., often greater than 100,000 receptors/cell), whereas the receptor expression for ErbB3 and ErbB4 ranges from between 5,000 to 20,000 receptors/cell. A bsBA that antagonizes ligand binding will successfully inhibit receptor signaling even though the receptor expression levels differ more than 10 fold.

Our in silico analysis confirms the effectiveness of a bispecific ErbB1/ErbB3 and ErbB1/ErbB4 bsBA. The inhibition of the ErbB3 receptor inhibits signaling in a HRG dominated regime.

Based on our in silico analysis of the ErbB cell signaling pathway, we identified the ErbB1 binding molecule as the high affinity binding site with a low dissociation constant $K_D < 1$ nM, but which is not irreversible. ErbB3 and ErbB4 receptors are expressed at much lower levels than ErbB1 receptors. Because the bsBA binds to both ErB1 and ErbB3/ErbB4 receptors, and because the bsBA has a higher affinity for the more abundant ErbB1 receptor, the bsBA can effectively block cell signaling mediated by dimerization of ErbB1 with either ErbB3 or ErbB4 at a much lower concentration than conventional monospecific ErbB inhibitors. The high affinity of the bsBA for ErbB1 leads to a high efficiency at low bsBA concentrations.

Our approach takes advantage of computational modeling to identify the optimal receptors for cross linking as well as the desired affinities of the two binding molecules. The differential affinity of the two binding molecules of the bsBA effectively target the bsBA to receptors, such as ErbB3, that are not thought to be specific to cancer cells. Cross-linking ErbB3 to a more typical cancer antigen such as ErbB1 provides a means to specifically target cancer cells and to modulate ErbB3 receptor activity in these cells.

Using our computational model, we identified the necessity for the differential affinity of the two binding molecules of the bsBA. The differential affinity promotes stabilization of the bsBA trimer complex. Generally speaking, the active binding molecule of the bsBA should have the lower affinity compared to the inactive or less active binding molecule. If both binding molecules of the bsBA are inactive or less active, the binding molecule targeting the higher expressed or stronger signaling receptor should have the higher affinity. Having a differential affinity for one of the receptors targeted results in the following: if the bsBA is administered at a concentration above the Kd of higher affinity interaction (e.g. ErbB1), but below the Kd of lower affinity interaction (e.g. ErbB3) the bsBA should only accumulate onto cells expressing the antigen for the higher affinity interaction. The other end of the bsBA is available to interact with the low affinity antigen on these cells to interfere with its biological function (e.g. ErbB3; to prevent downstream signaling). Which receptor will be the low or high affinity interaction depends on the receptor's specific signaling strength (importance as a target) and the mode of action of the bsBA.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating a malignancy comprising administering to a patient an effective amount of a bispecific binding agent capable of modulating biological activity of target cancer cells that have a first and a second target antigen on their exterior surface, wherein (i) said first and second target-antigens do not share a common ligand,
(ii) said second target antigen is a receptor tyrosine kinase, and
(iii) said bispecific binding agent has a first binding domain that is an antibody that binds to the first target antigen with a dissociation constant (Kd) for the first target antigen of $10^{-7}$ M or less and a second binding domain that is an antibody that binds to the second target antigen with a Kd for the second target antigen that is at least 10 times greater than the Kd of the first binding domain, and when the first target antigen of said first binding domain is ErbB2 (HER2), the second target antigen for said second binding domain is not ErbB3 (HER3); and,
wherein said binding of said first antigen to said first binding domain does not modulate biological activity of said first target antigen, but said binding of said second binding domain to said second target antigen modulates the biological activity of said second target antigen, and the biological activity results in either an inhibition of target cell proliferation or death of the target cell.

2. A method of claim 1, wherein the antibodies are diabodies, single chain Fvs, disulfide stabilized Fvs, or combinations thereof, and are connected directly or by a linker.

3. A method of claim 1, wherein the second target antigen is a tumor-associated antigen, cytokine receptor, or growth factor receptor.

4. A method of claim 1, wherein said first target antigen is selected from the group consisting of carcinoembryonic antigen (CEA), ErbB2, EGFR, Lewis$^Y$, MUC-1, EpCAM, CA125, prostate specific membrane antigen (PSMA), and TAG72.

5. A method of claim 1, wherein the second target antigen is selected from the group consisting of ErbB3, ErbB4, any of FGF receptors 1-4, HGF receptor, IGF1-R, PDGF receptors alpha and beta, and C-KIT.

6. A method of claim 1, wherein the Kd of the first binding domain for the first target antigen is between $10^{-8}$ M and $10^{-12}$ M.

7. A method of claim 1, wherein the Kd of the second binding domain to the second target antigen is at least 20 times greater than the Kd of the first binding domain to the first target antigen.

8. A method of claim 1, wherein the Kd of the second binding domain to the second target antigen is at least 50 times greater than the Kd of the first binding domain to the first target antigen.

9. A method of claim 1 wherein the patient is a human patient, and the target cell is a cell in the patient.

* * * * *